US006815169B1

(12) United States Patent
Sakowicz et al.

(10) Patent No.: US 6,815,169 B1
(45) Date of Patent: Nov. 9, 2004

(54) IDENTIFICATION AND EXPRESSION OF A NOVEL KINESIN MOTOR PROTEIN

(75) Inventors: Roman Sakowicz, Foster City, CA (US); Lawrence S. B. Goldstein, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 75 days.

(21) Appl. No.: 09/724,666

(22) Filed: Nov. 28, 2000

Related U.S. Application Data

(62) Division of application No. 09/235,416, filed on Jan. 22, 1999.
(60) Provisional application No. 60/072,361, filed on Jan. 23, 1998.

(51) Int. Cl.[7] .................. G01N 33/53; G01N 33/569; G01N 33/537; G01N 33/543; G01N 33/542
(52) U.S. Cl. ................ 435/7.1; 424/9.34; 424/9.6; 424/130.1; 424/137.1; 424/139.1; 424/184.1; 424/185.1; 424/278.1; 435/4; 435/6; 435/7.31; 435/7.37; 435/7.7; 435/7.8; 435/7.9; 435/7.92; 435/7.93; 435/7.94; 435/7.95; 435/29; 435/32; 435/34; 435/174; 435/254.1; 435/333; 435/340; 435/341; 436/501; 436/512; 436/513; 436/546; 436/547; 436/548; 530/371
(58) Field of Search .................. 435/7.1, 7.37, 435/7.7, 7.71, 7.8, 7.9, 7.92, 7.93, 7.94, 7.95, 29, 32; 436/501, 512, 513, 546, 547, 548; 530/371

(56) References Cited

U.S. PATENT DOCUMENTS

| | | | |
|---|---|---|---|
| 4,366,241 A | 12/1982 | Tom | 435/7.91 |
| 4,376,110 A | 3/1983 | David | 435/5 |
| 4,391,904 A | 7/1983 | Litman | 435/7.91 |
| 4,469,863 A | 9/1984 | Ts'o | 536/24.5 |
| 4,517,288 A | 5/1985 | Giegel | 435/5 |
| 4,683,195 A | 7/1987 | Mullis | 435/6 |
| 4,683,202 A | 7/1987 | Mullis | 435/91.2 |
| 4,736,866 A | 4/1988 | Leder | 800/10 |
| 4,816,567 A | 3/1989 | Cabilly | 530/387.3 |
| 4,837,168 A | 6/1989 | de Jaeger | 436/533 |
| 4,870,009 A | 9/1989 | Evans | 435/69.4 |
| 5,034,506 A | 7/1991 | Summerton | 528/391 |
| 5,216,141 A | 6/1993 | Benner | 536/27.13 |
| 5,235,033 A | 8/1993 | Summerton | 528/391 |
| 5,283,173 A | 2/1994 | Fields | 435/6 |
| 5,386,023 A | 1/1995 | Sanghvi | 536/25.3 |
| 5,468,614 A | 11/1995 | Fields | 435/6 |
| 5,525,490 A | 6/1996 | Erickson | 435/9 |
| 5,545,806 A | 8/1996 | Lonberg | 800/6 |
| 5,545,807 A | 8/1996 | Surani | 800/6 |
| 5,569,825 A | 10/1996 | Lonberg | 800/18 |
| 5,602,240 A | 2/1997 | De Mesmaeker | 536/22.1 |
| 5,625,126 A | 4/1997 | Lonberg | 800/18 |
| 5,633,425 A | 5/1997 | Lonberg | 800/18 |
| 5,637,463 A | 6/1997 | Dalton | 435/6 |
| 5,637,684 A | 6/1997 | Cook | 536/23.1 |
| 5,644,048 A | 7/1997 | Yau | 536/25.3 |
| 5,661,016 A | 8/1997 | Lonberg | 435/452 |
| 5,667,973 A | 9/1997 | Fields | 435/6 |

FOREIGN PATENT DOCUMENTS

| | | | |
|---|---|---|---|
| WO | 93/08829 | 5/1993 | A61K/37/04 |
| WO | 95/18857 | 7/1995 | C12N/15/12 |

OTHER PUBLICATIONS

Alphey et al. 1997. J. of Cell Bio. 138(2): 395–409.*
Blangy et al. 1997. J. of Biol. Chem. 272(21):19418–19424.*
Goldstein. 1993. Annu. Rev. genet. 27:319–51.*
Nangaku et al. 1994. Cell. 79:1209–2220.*
Sekine et al. 1994. J. of Cell Bio. 127(1):187–201.*
Akerstrom et al., "Protein G: a powerful tool for binding and detection of monoclonal and polyclonal antibodies," *J Immunol.* 135:2589–92 (1985).
Altschul et al., "Basic local alignment search tool," *J Mol Biol.* 215:403–10 (1990).
Batzer et al., "Enhanced evolutionary PCR using oligonucleotides with inosine at the 3'–terminus," *Nucleic Acids Res.* 19:5081 (1991).
Beaucage and Caruthers, "Optimistic about antisense," *Tetrahedron Letts* 22:1859–1862 (1981).
Beaucage and Iyer, "The functionalization of oligonucleotides via phosphoramidite derivatives," *Tetrahedron* 49:1925 (1993).
Benton and Davis, "Screening lambdagt recombinant clones by hybridization to single plaques in situ," *Science.* 196:180–2 (1977).
Boerner et al., "Production of antigen–specific human monoclonal antibodes from in vitro–primed human splenocytes," *J Immunol.* 147:86–95 (1991).
Bradley, "Production and analysis of chimeric mice," *Teratocarcinomas and Embryonic Stem Cells: A Practical Approach* Robertson (ed.) Oxford: IRL Press Limited, pp. 113–152 (1987).
Brill et al., "Synthesis of oligodeoxynucleoside phosphorodithioates via thioamidites," *J Am Chem Soc* 111:2321–2322 (1989).
Chien et al., "The two–hybrid system: a method to identify and clone genes for proteins that interact with a protein of interest," *Proc Natl Acad Sci U S A.* 88:9578–82 (1991).
Clark–Curtiss and Curtiss, "Analysis of recombinant DNA using *Eschericia coli* minicells," in *Method Enzymol.* Wu et al., (eds.) 101:347–62 (1983).

(List continued on next page.)

*Primary Examiner*—Lynette R. F. Smith
*Assistant Examiner*—J. Hines
(74) *Attorney, Agent, or Firm*—Medlen & Carroll, LLP

(57) ABSTRACT

The invention provides isolated nucleic acid and amino acid sequences of TL-γ, antibodies to TL-γ, methods of screening for TL-γ modulators using biologically active TL-γ, and kits for screening for TL-γ modulators.

20 Claims, No Drawings

OTHER PUBLICATIONS

Cole et al., "The EBV–hybridoma technique and its application to human lung cancer," in *Monoclonal Antibodies and Cancer Therapy*, Reisfeld et al. (eds). pp. 77–96, Alan R. Liss,Inc. (1985).

Colley et al., "Conversion of a Golgi apparatus sialyltransferase to a secretory protein by replacement of the NH2–terminal signal anchor with a signal peptide," *J Biol Chem.* 264:17619–22 (1989).

Dang et al., "Intracellular leucine zipper interactions suggest c–Myc hetero–oligomerization," *Mol. Cell Biol.* 11:954–62 (1991).

DeMesmaeker et al., "Comparison of rigid and flexible backbones in antisense oligonucleotides," *Bioorganic and Medicinal Chem Lett* 4:395–398 (1994).

Dempey et al., "Synthesis of a thymidyl pentamer of deoxyribonucleic guanidine and binding studies with DNA homopolynucleotides," *Proc Natl Acad Sci U S A.* 92:6097–101 (1995).

Egholm et al., "Peptide nucleic–acids (pna): oligonucleotide analogs with an achiral peptide backbone," *J Am Chem Soc* 114:1895–1897 (1992).

Fearon et al., "Karyoplasmic interaction selection strategy: a general strategy to detect protein–protein interactions in mammalian cell," *Proc Natl Acad Sci U S A.* 89:7958–62 (1992).

Feng and Doolittle, "Progressive sequence alignment as a prerequisite to correct phylogenetic trees," *J Mol Evol.*25:351–60 (1987).

Fields and Song, "A novel genetic system to detect protein––protein interactions," *Nature.* 340:245–6 (1989).

Fishwild et al., "High–avidity human IgG kappa monoclonal antibodes from a novel strain of minilocus transgenic mice," *Nat Biotechnol.* 14:845–51 (1996).

Gao and Jeffs, "Unusual conformation of a 3'–thioformacetal linkage in a DNA duplex," *J Biol NRM.* 4:17–34 (1994).

Grunstein and Hogness, "Colony hybridization: a method for the isolation of cloned DNAs that contain a specific gene," *Proc Natl Acad Sci U S A* 72:3961–5 (1975).

Gubler and Hoffman, "A simple and very efficient method for generating cDNA libraries," *Gene* 25(2–3):263–9 (1983).

Haase et al., "Detection of viral nucleic acids by in situ hybridization," *Methods in Virology* 7:189–226 (1984).

Hackney et al., "Nucleotide–free kinesin hydrolyzes ATP with burst kinetics," *J Biol Chem* 264:15943–8 (1989).

Henikoff and Henikoff, "Amino acid substitution matrices from protein blocks," *Proc Natl Acad Sci U S A* 89:10915–9 (1992).

Higgins and Sharp, "Fast and sensitive multiple sequence alignments on a microcomputer," *Comput Appl Biosci* 5(2):151–3 (1989).

Hoogenboom and Winter, "By–passing immunisation. Human antibodies from synthetic repertoires of germline VH gene segments rearranged in vitro," *J Mol Biol* 227:381–8 (1992).

Horn et al., "Oligonucleotides with alternating anionic and cationic phosphoramidate linkages: Synthesis and hybridization of stereo–uniform isomers," *Tetrahedron Letters* 37:743–746 (1996).

Howard et al., in *Motility Assays for Motor Proteins* Scholey (ed.) San Diego: Academic Press, pp. 105–113 (1993).

Huse et al., "Generation of a large combinatorial library of the immunoglobulin repertoire in phage lambda," *Science* 246:1275–8 (1989).

Hyman et al., "Preparation of modified tubulins," *Methods Enzymol* 196:478–85 (1991).

Jenkins and Turner, "The biosynthesis of carbocyclic nucleosides," *Chem Soc Rev* 24:169–176 (1995).

Jones et al., "Replacing the complementarity–determining regions in a human antibody with those from a mouse, "*Nature* 321:522–5 (1986).

Jung et al., "Hybridization of alternating cationic/anionic oligonucleotides to rna segments," *Nucleosides & Nucleotides* 13:1597–1605 (1994).

Karlin and Altschul, "Applications and statistics for multiple high–scoring segments in molecular sequences,"*Proc Natl Acad Sci U S A* 90:5873–7 (1993).

Kishino and Yanagido, "Force measurements by micromanipulation of a single actin filament by glass needles," *Nature* 334:74–6 (1988).

Kodama et al., "The initial phosphate burst in ATP hydrolysis by myosin and subfragment–1 as studied by a modified malachite green method for determination of inorganic phosphate," *J Biochem (Tokyo)* 99:1465–72 (1986).

Kohler and Milstein, "Continuous cultures of fused cells secreting antibody of predefined specificity," *Nature* 256:495–7 (1975).

Kohler and Milstein, "Derivation of specific antibody–producing tissue culture and tumor lines by cell fusion," *Eur J Immunol* 6:511–9 (1976).

Kronvall, "A surface component in group A, C, and G streptococci with non–immune reactivity G," *J Immunol* 111:1401–6 (1973).

Letsinger and Mungall, "Phosphoramidate analogs of oligonucleotides," *J Org Chem* 35:3800–3 (1970).

Letsinger et al., "Effects of pendant groups at phosphorus on binding properties of d–ApA analogue," *Nucleic Acids Res* 14:3487–99 (1986).

Letsinger et al., "Cationic oligonucleotides," *J Am Chem Soc* 110:4470 (1988).

Li et al., "Targeted mutation of the DNA methyltransferase gene results in embryonic lethality," *Cell* 69:915–26 (1992).

Lombillo et al., "Antibodies to the kinesin motor domain and CENP–E inhibit microtubule depolymerization–dependent motion of chromosomes in vitro," *J Cell Biol* 128:107–15 (1995).

Lonberg et al., "Antigen–specific human antibodies from mice comprising four distinct genetic modifications," *Nature* 368:856–9 (1994).

Mag et al., "Synthesis and selective cleavage of an oligodeoxynucleotide containing a bridged internucleotide 5'–phosphorothioate linkage," *Nucleic Acids Res* 19:1437–41 (1991).

Marks et al., "By–passing immunization. Human antibodies from V–gene libraries displayed on phage," *J Mol Biol* 222:581–97 (1991).

Marks et al., "By–passing immunization: Building high affinity human antibodies by chain shuffling," *Biotechnology* 10:779–83 (1992).

Meier and Engels, "Peptide nucleic–acids (pnas): unusual properties of nonionic oligonucleotide analogs," *Angewandete Chemie (Int Ed Engl)* 31:1008–1010 (1992).

Milstein and Cuello, "Hybrid hybridomas and their use in immunohistochemistry," *Nature* 305:537–40 (1983).

Morrison, "Transformation in *Escherichia coli:* cryogenic preservation of competent cells," *J Bacteriol* 132:349–51 (1977).

Morrison, "Immunology. Success in specification," *Nature* 368:812–3 (1994).

Mosbach et al., "Formation of proinsulin by immobilized *Bacillus subtilis,*" *Nature* 302:543–5 (1983).

Nazar and Wong, Is the 5S RNA a primitive ribosomal sequence? *Proc Natl Acad Sci U S A* 82:5608–11 (1985).

Needham–VanDevanter et al., "Characterization of an adduct between CC–1065 and a defined oligodeoxynucleotide duplex," *Nucleic Acids Res* 12:6159–68 (1984).

Needleman and Wunsch, "A general method applicable to the search for similarities in the amino acid sequence of two proteins," *J Mol Biol* 48:443–53 (1970).

Neuberger, "Generating high–avidity human Mabs in mice," *Nat Biotechnol* 14:826 (1996).

Ohtsuka et al., "An alternative approach to deoxyoligonucleotides as hybridization probes by insertion of deoxyinosine at ambiguous codon positions," *J Biol Chem* 260:2605–8 (1985).

Palva et al., "Secretion of interferon by *Bacillus subtilis,*" *Gene* 22:229–35 (1983).

Pauwels et al., "Biological–activity of new 2–5a analogs," *Chemica Scripta* 26:141–145 (1986).

Pearson and Lipman, "Improved tools for biological sequence comparison," *Proc Natl Acad Sci U S A* 85:2444–8 (1988).

Pearson and Reanier, "High–performance anion–exchange chromaotgraphy of oligonucleotides," *J Chrom* 255:137–149 (1983).

Presta, "Antibody engineering," Curr Opin Struct Biol 2:593–596 (1992).

Rawls, "Optimistic about antisense," *Chemical & Engineering News* 75:35–39 (1997).

Riechmann et al., "Reshaping human antibodies for therapy," *Nature* 332:323–7 (1988).

Rossolini et al., "Use of deoxyinosine–containing primers vs degenerate primers for polymerase chain reaction based on ambiguous sequence information," *Mol Cell Probes* 8:91–8 (1994).

Singer et al., "Optimization of in situ hybridization using isotopic and non–isotopic detection methods," *Biotechniques* 4:230–250 (1986).

Smith and Waterman, "Comparison of biosequences," *Adv Appl Math* 2:482 (1981).

Sprinzl et al., "Enzymatic incorporation of ATP and CTP analogues into the 3' end of tRNA," *Eur J Biochm* 81:579–89 (1977).

Stewart et al., "Direction of microtubule movement is an intrinsic property of the motor domains of kinesin heavy chain and Drosphila ned protein," *Proc Natl Acad Sci U S A* 90:5209–13 (1993).

Suresh et al., "Bispecific monoclonal antibodes from hybrid hybridomas," *Methods Enzymol* 121:210–28 (1986).

Thomas and Capecchi, "Site–directed mutagenesis by gene targeting in mouse embryo–derived stem cells." *Cell* 51:503–12 (1987).

Traunecker et al., "Bispecific single chain molecules (Janusins) target cytotoxic lymphocytes on HIV infected cells," *EMBO J* 10:3655–9 (1991).

Vale et al., "Identification of a novel force–generating protein, kinesin, involved in microtubule–based motility," *Cell* 42:39–50 (1985).

Vasavada et al., "A contingent replication assay for the detection of protein–protein interactions in animal cells," *Proc Natl Acad Sci U S A* 88:10686–90 (1991).

Verhoeyen et al., "Reshaping human antibodies: grafting an antilysozyme activity," *Science* 239:1534–6 (1988).

Vonkiedrowski et al., "Parabolic growth of a self–replicating hexadeoxynucleotide bearing a 3',5'–phosphoamidate linkage," *Angewandte Chemie–International Edition in English* 30:423–426 (1991).

Wallace et al., "A set of synthetic oligodeoxyribonucleotide primers for DNA sequencing in the plasmid vector pBR322," *Gene* 16:21–6 (1981).

Ward et al., "Binding activities of a repertoire of single immunoglobulin variable domains secreted from *Escherichia coli,*" *Nature* 341(6242):544–6 (1989).

Zamecnik et al., "Inhibition of replication and expression of human T–cell lymphotropic virus type III in cultured cells by exogenous synthetic oligonucleotides complementary to viral RNA," *Proc Natl Acad Sci U S A.* 83:4143–6 (1986).

Aizawa et al., "Kinesin family in murine central nervous system," *J Cell Biol.* 119:1287–96 (1992).

Alphey et al., "KLP38B: a mitotic kinesin–related protein that binds PP1," *J Cell Biol.* 138:395–409 (1997).

Blangy et al., "Phosphorylation by p34cdc2 protein kinase regulates binding of the kinesin–related motor HsEg5 to the dynactin subunit p150," *J Biol Chem* 272:19418–24 (1997).

Furlong et al., "Characterization of a kinesin–related gene ATSV, within the tuberous sclerosis locus (TSCl) candidate region on chromosome 9Q34," *Genomics* 33:421–9 (1996).

Goldstein, "With apologies to scheherazade: tails of 1001 kinesin motors," *Annu Rev Genet.* 27:319–51 (1993).

Li et al., "Kinesin–73 in the nervous system of Drosophila embryos," *Proc Natl Acad Sci U S A* 94:1086–9 (1997).

Nangaku et al., "KIF1B, a novel microtubule plus end–directed monomeric motor protein for transport of mitochondria," *Cell* 79:1209–20 (1994).

O'Connell et al., "Suppression of the bimC4 mitotic spindle defect by deletion of klpA, a gene encoding a KAR3–related kinesin–like protein in Aspergillus nidulans," *J Cell Biol.* 120:153–62 (1993).

Okada et al., "The neuron–specific kinesin superfamily protein KIF1A is a unique monomeric motor for anterograde axonal tansport of synaptic vesicle precursors," *Cell* 81:769–80 (1995).

Oppenheimer et al., "Essential role of a kinesin–like protein in Arabidopsis trichome morphogenesis," *Proc Natl Acad Sci U S A.* 94:6261–6 (1997).

Otsuka et al., "The C. elegans unc–104 gene encodes a putative kinesin heavy chain–like protein," *Neuron* 6:113–22 (1991).

Prekeris and Terrian, "Brain mysoin V is a synaptic vesicle–associated motor protein: evidence for a Ca2+–dependent interaction with the synaptobrevin–synaptophysin complex," *J Cell Biol.* 137:1589–601 (1997).

Sekine et al., "A novel microtubule–based motor protein (KIF4) for organelle transports, whose expression is regulated developmentally," *J Cell Biol.* 127:187–201 (1994).

\* cited by examiner

SEQUENCE LISTING

```
<160> NUMBER OF SEQ ID NOS: 7

<210> SEQ ID NO 1
<211> LENGTH: 784
<212> TYPE: PRT
<213> ORGANISM: Thermomyces lanuginosus
<220> FEATURE:
<223> OTHER INFORMATION: TL-gamma ATP-dependent plus end-directed
      microtubule motor protein
<220> FEATURE:
<221> NAME/KEY: DOMAIN
<222> LOCATION: (1)..(357)
<223> OTHER INFORMATION: kinesin-like microtubule motor domain
<220> FEATURE:
<221> NAME/KEY: DOMAIN
<222> LOCATION: (358)..(442)
<223> OTHER INFORMATION: neck domain links motor domain to stalk domain
<220> FEATURE:
<221> NAME/KEY: DOMAIN
<222> LOCATION: (443)..(601)
```

```
<223> OTHER INFORMATION: stalk domain, unc-104 family domain
<220> FEATURE:
<221> NAME/KEY: DOMAIN
<222> LOCATION: (602)..(784)
<223> OTHER INFORMATION: tail domain

<400> SEQUENCE: 1

Met Ser Gly Gly Gly Asn Ile Lys Val Val Arg Val Arg Pro Phe
  1               5                  10                  15

Asn Ala Arg Glu Ile Asp Arg Gly Ala Lys Cys Ile Val Arg Met Glu
             20                  25                  30

Gly Asn Gln Thr Ile Leu Thr Pro Pro Gly Ala Glu Glu Lys Ala
         35                  40                  45

Arg Lys Ser Gly Lys Thr Ile Met Asp Gly Lys Ala Phe Ala Phe
     50                  55                  60

Asp Arg Ser Tyr Trp Ser Phe Asp Lys Asn Ala Pro Asn Tyr Ala Arg
 65                  70                  75                  80

Gln Glu Asp Leu Phe Gln Asp Leu Gly Val Pro Leu Leu Asp Asn Ala
                 85                  90                  95

Phe Lys Gly Tyr Asn Asn Cys Ile Phe Ala Tyr Gly Gln Thr Gly Ser
            100                 105                 110

Gly Lys Ser Tyr Ser Met Met Gly Tyr Gly Lys Glu His Gly Val Ile
            115                 120                 125

Pro Arg Ile Cys Gln Asp Met Phe Arg Arg Ile Asn Glu Leu Gln Lys
            130                 135                 140

Asp Lys Asn Leu Thr Cys Thr Val Glu Val Ser Tyr Leu Glu Ile Tyr
145                 150                 155                 160

Asn Glu Arg Val Arg Asp Leu Leu Asn Pro Ser Thr Lys Gly Asn Leu
                165                 170                 175

Lys Val Arg Glu His Pro Ser Thr Gly Pro Tyr Val Glu Asp Leu Ala
            180                 185                 190

Lys Leu Val Val Arg Ser Phe Gln Glu Ile Glu Asn Leu Met Asp Glu
            195                 200                 205

Gly Asn Lys Ala Arg Thr Val Ala Ala Thr Asn Met Asn Glu Thr Ser
210                 215                 220

Ser Arg Ser His Ala Val Phe Thr Leu Thr Leu Thr Gln Lys Trp His
225                 230                 235                 240

Asp Glu Glu Thr Lys Met Asp Thr Glu Lys Val Ala Lys Ile Ser Leu
                245                 250                 255

Val Asp Leu Ala Gly Ser Glu Arg Ala Thr Ser Thr Gly Ala Thr Gly
            260                 265                 270

Ala Arg Leu Lys Glu Gly Ala Glu Ile Asn Arg Ser Leu Ser Thr Leu
            275                 280                 285

Gly Arg Val Ile Ala Ala Leu Ala Asp Met Ser Ser Gly Lys Gln Lys
            290                 295                 300

Lys Asn Gln Leu Val Pro Tyr Arg Asp Ser Val Leu Thr Trp Leu Leu
305                 310                 315                 320

Lys Asp Ser Leu Gly Gly Asn Ser Met Thr Ala Met Ile Ala Ala Ile
                325                 330                 335

Ser Pro Ala Asp Ile Asn Phe Glu Thr Leu Ser Thr Leu Arg Tyr
            340                 345                 350

Ala Asp Ser Ala Lys Arg Ile Lys Asn His Ala Val Val Asn Glu Asp
            355                 360                 365

Pro Asn Ala Arg Met Ile Arg Glu Leu Lys Glu Glu Leu Ala Gln Leu
            370                 375                 380
```

-continued

```
Arg Ser Lys Leu Gln Ser Gly Gly Gly Gly Ala Gly Gly
385                 390                 395                 400

Ser Gly Gly Pro Val Glu Ser Tyr Pro Pro Asp Thr Pro Leu Glu
            405                 410                 415

Lys Gln Ile Val Ser Ile Gln Pro Asp Ala Thr Val Lys Lys Met
            420                 425                 430

Ser Lys Ala Glu Ile Val Glu Gln Leu Asn Gln Ser Glu Lys Leu Tyr
        435                 440                 445

Arg Asp Leu Asn Gln Thr Trp Glu Glu Lys Leu Ala Lys Thr Glu Glu
    450                 455                 460

Ile His Lys Glu Arg Glu Ala Leu Glu Glu Leu Gly Ile Ser Ile
465                 470                 475                 480

Glu Lys Gly Phe Val Gly Pro Tyr His Ser Lys Glu Met Pro His Leu
            485                 490                 495

Val Asn Leu Ser Asp Asp Pro Leu Leu Ala Glu Cys Leu Val Tyr Asn
            500                 505                 510

Ile Lys Pro Gly Gln Thr Arg Val Gly Asn Val Asn Gln Asp Thr Gln
        515                 520                 525

Ala Glu Ile Arg Leu Asn Gly Ser Lys Ile Leu Lys Glu His Cys Thr
    530                 535                 540

Phe Glu Asn Val Asp Asn Val Val Thr Ile Val Pro Asn Glu Lys Ala
545                 550                 555                 560

Ala Val Met Val Asn Gly Val Arg Ile Asp Lys Pro Thr Arg Leu Arg
            565                 570                 575

Ser Gly Tyr Arg Ile Ile Leu Gly Asp Phe His Ile Phe Arg Phe Asn
            580                 585                 590

His Pro Glu Glu Ala Arg Ala Glu Arg Gln Glu Gln Ser Leu Leu Arg
        595                 600                 605

His Ser Val Thr Asn Ser Gln Leu Gly Ser Pro Ala Pro Gly Arg His
    610                 615                 620

Asp Arg Thr Leu Ser Lys Ala Gly Ser Asp Ala Asp Gly Asp Ser Arg
625                 630                 635                 640

Ser Asp Ser Pro Leu Pro His Phe Arg Gly Lys Asp Ser Asp Trp Phe
            645                 650                 655

Tyr Ala Arg Arg Glu Ala Ala Ser Ala Ile Leu Gly Leu Asp Gln Lys
            660                 665                 670

Ile Ser His Leu Thr Asp Asp Glu Leu Asp Ala Leu Phe Asp Asp Val
        675                 680                 685

Gln Lys Ala Arg Ala Val Arg Arg Gly Leu Val Glu Asp Asn Glu Asp
    690                 695                 700

Ser Asp Ser Gln Ser Ser Phe Pro Val Arg Asp Lys Tyr Met Ser Asn
705                 710                 715                 720

Gly Thr Ile Asp Asn Phe Ser Leu Asp Thr Ala Ile Thr Met Pro Gly
            725                 730                 735

Thr Pro Arg Ser Asp Asp Gly Asp Ala Leu Phe Phe Gly Asp Lys
            740                 745                 750

Lys Ser Lys Gln Asp Ala Ser Asn Val Asp Val Glu Glu Leu Arg Gln
        755                 760                 765

Gln Gln Ala Gln Met Glu Glu Ala Leu Lys Thr Ala Lys Gln Glu Phe
    770                 775                 780
```

<210> SEQ ID NO 2
<211> LENGTH: 2352

<212> TYPE: DNA
<213> ORGANISM: Thermomyces lanuginosus
<220> FEATURE:
<223> OTHER INFORMATION: TL-gamma ATP-dependent plus end-directed microtubule motor protein

<400> SEQUENCE: 2

```
atgtcgggcg gtggaaatat caaggtggtg gtgcgggtac gcccgttcaa cgcccgagaa      60
atcgaccgtg gcgcaaaatg tattgtgcgg atggaaggaa atcaaaccat cctcacccct     120
cctccgggtg ccgaagagaa ggcgcgtaaa agtggcaaaa ctattatgga tggcccgaag     180
gcatttgcgt tcgatcggtc gtattggtcc tttgacaaga atgctcccaa ctatgcgaga     240
caggaagacc tattccaaga tctcggagtc ccgcttctgg ataatgcatt caagggttat     300
aacaattgta tcttcgccta cggtcagacc ggttcgggca agtcctattc aatgatgggc     360
tatggcaagg agcatggcgt gatcccgcgg atttgccagg acatgttccg gcgtattaat     420
gaactgcaga aggacaagaa cctcacttgc accgtcgaag tttcgtactt ggaaatttac     480
aatgaacgag tgcgagactt gctgaatccg tcgacaaagg ggaatctcaa ggtccgagaa     540
cacccgtcga ccgccccta cgtggaggac ttggcgaagc tggtcgtgcg atcattccaa     600
gaaatcgaaa atctcatgga tgagggcaac aaagccagaa cggttgccgc cacaaacatg     660
aacgagacat ccagtcgatc ccacgccgtc ttcactttga ccttgacgca aaagtggcat     720
gatgaagaga ccaaaatgga cacagagaag gttgcgaaga tcagtctggt agatttggcg     780
ggttctgagc gagcaacgtc caccggagct actggagcgc gactgaagga gggtgcagag     840
atcaaccgct cactttcgac cctaggtcgt gtgattgcag cgctagcgga tatgtcgtcg     900
ggaaaacaga agaagaatca gttagtacct taccgagatt cggtactgac gtggcttctg     960
aaggactcct tgggaggcaa ctcgatgacc gccatgattg ccgccatttc gcctgctgat    1020
attaactttg aagagactct cagtaccctt cgatatgcgg actctgcgaa gcgaatcaag    1080
aaccacgcag tggtcaatga agacccgaac gcgcggatga tccgcgagtt gaaggaggaa    1140
ctcgcgcagc tgaggagcaa actccagagc agtggtggag gtggaggtgg tgcaggaggt    1200
tctggcgggc cagtggagga atcgtacccg cccgacacgc cgctcgagaa gcaaatcgtg    1260
tcgattcagc agccggatgc gacagtcaag aaaatgagca aggcagaaat cgtggagcaa    1320
ctgaaccaga gtgagaagct ctatcgggat ctcaatcaga cctgggaaga gaagctggcc    1380
aagaccgagg aaatccacaa ggaacgagaa gcggcgctcg aggagctggg tatcagcatc    1440
gaaaagggct tgttggccc ttaccactcc aaagaaatgc cacatctagt caacttgagc    1500
gatgatcctc ttctggctga gtgtcttgtc tacaacatca gcccgggca gacaagggtt    1560
ggaaacgtca accaagatac acaagcggaa attcgtctga acggttcgaa gatcctgaaa    1620
gaacactgta cgtttgaaaa tgtggacaac gttgtgacca tcgtgccaaa cgagaaggct    1680
gctgtcatgg tgaacggcgt gcgaatcgac aagcctactc gcctccgcag cggctacagg    1740
atcatcctgg gcgatttcca cattttttga ttcaaccatc cggaagaagc tcgtgcggaa    1800
cggcaagaac aatccttgct cgccattct gtcaccaaca gtcagttggg ttcgcctgct    1860
ccaggccgtc acgaccggac actgagcaag gcgggttcgg atgcggacgg cgattctcgc    1920
tcagattctc ctttgccgca ctttcgtgga aggatagcg actggttcta tgctcgcagg    1980
gaagctgcta gcgcgatcct agggttggat cagaagatct ctcatctgac agatgacgag    2040
ttggatgcat tatttgacga tgttcagaaa gcgcgggcag ttcgtcgtgg gctggtcgaa    2100
gacaacgaag atagcgattc gcagagttcg tttccggtcc gtgacaaata catgtccaat    2160
```

```
ggaaccattg ataatttctc gctcgatacc gccattacta tgccgggtac ccctcgtagt    2220
gatgacgacg gtgacgcgct gttttttggt gataagaagt cgaaacagga tgcgtctaat    2280
gttgatgttg aggagttgcg tcaacagcag gctcagatgg aagaagccct gaaaacagcg    2340
aagcaggaat tc                                                        2352
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 3
atgtcgggcg gtggaaatat c                                              21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 4
gaattcctgc ttcgctgttt tca                                            23

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:degenerate
      forward primer
<220> FEATURE:
<221> NAME/KEY: modified_base
<222> LOCATION: (25)
<223> OTHER INFORMATION: n = a, c, g or t

<400> SEQUENCE: 5
gcgcggatcc atyttygcht ayggncarac                                     30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:degenerate
      reverse primer
<220> FEATURE:
<221> NAME/KEY: modified_base
<222> LOCATION: (16)
<223> OTHER INFORMATION: n = a, c, g or t
<220> FEATURE:
<221> NAME/KEY: modified_base
<222> LOCATION: (28)
<223> OTHER INFORMATION: n = a, c, g or t

<400> SEQUENCE: 6
gcgcgaattc tcdganccdg cvarrtcnac                                     30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:degenerate
      reverse primer
```

```
<220> FEATURE:
<221> NAME/KEY: modified_base
<222> LOCATION: (16)
<223> OTHER INFORMATION: n = a, c, g or t
<220> FEATURE:
<221> NAME/KEY: modified_base
<222> LOCATION: (28)
<223> OTHER INFORMATION: n = a, c, g or t

<400> SEQUENCE: 7
gcgcgaattc tcdctnccdg cvarrtcnac                                    30
```

US 6,815,169 B1

IDENTIFICATION AND EXPRESSION OF A NOVEL KINESIN MOTOR PROTEIN

CROSS REFERENCE TO RELATED APPLICATIONS

This is a Divisional of application Ser. No. 09/235,416, filed Jan. 22, 1999, which claims benefit under 35 U.S.C. §119(e) to Provisonal Patent Ser. No. 60/072,361, filed on Jan. 23, 1998, which is herein incorporated by reference in its entirety for all purposes.

FEDERALLY SPONSORED RESEARCH OR DEVELOPMENT

This invention was made with Government support under Grant No. GM35252, awarded by the National Institutes of Health, and Grant No. DMR 9612252, awarded by the National Science Foundation. The Government has certain rights in this invention.

FIELD OF THE INVENTION

The invention provides isolated nucleic acid and amino acid sequences of TL-$\gamma$, antibodies to TL-$\gamma$, methods of detecting TL-$\gamma$ and screening for TL-$\gamma$ modulators using biologically active TL-$\gamma$, and kits for screening for TL-$\gamma$ modulators.

BACKGROUND OF THE INVENTION

The kinesin superfamily is an extended family of related microtubule motor proteins. This family is exemplified by "true" kinesin, which was first isolated from the axoplasm of squid, where it is believed to play a role in anterograde axonal transport of vesicles and organelles (see, e.g., Goldstein, *Annu. Rev. Genet.* 27:319–351 (1993)). Kinesin uses ATP to generate force and directional movement associated with microtubules (from the minus to the plus end of the microtubule, hence it is a "plus-end directed" motor). Kinesin superfamily members are defined by a kinesin-like motor that is about 340 amino acids in size and shares approximately 35–45% identity (or more) with the "true" kinesin motor domain. Typically, the motor is attached to a variety of tail domains that provide different binding activities to the various kinesin superfamily members.

The kinesin superfamily encompasses a number of families that exhibit a variety of microtubule motor functions, e.g., vesicle and organelle transport, mitotic spindle function, and meiotic spindle function. One such family is the "unc-104 family" named after unc-104 protein in *C. elegans* (Otsuka et al., *Neuron* 6:13–122 (1991)). Other members of the unc-104 family include mouse Kif1A (murine homolog of unc-104) and Kif1B, and human ATSV (homolog of Kif1A) (Aizawa et al., *J. Cell Biol.*, 119:1287–1296 (1992); Okada et al., *Cell* 81:769–780 (1995); Nangaku et al., *Cell* 79:1209–1220 (1994); and Furlong et al., *Genomics* 33:421–429 (1996)). These proteins typically work as monomers, are ATP dependent, and have plus end-directed microtubule motor activity involved in fast anterograde organelle transport in neurons. Fast anterograde transport is a directional transport, typically of membranous organelles such as mitochondria, other organelles and vesicles such as synaptic vesicles, from the cell body to the tip of the axon. Members of the unc-104 family are not found in the first completely sequenced genome of *S. cerevisae*, and on this basis it was believed that fungi did not possess members of the unc-104 motor protein family.

Accordingly, among the objects of this invention is to provide novel members of the kinesin superfamily. It is particularly an object to provide novel kinesins and nucleic acids encoding such kinesins which have anterograde axonal transport activity, including novel members of the unc-104 family, indicated by example, by sequence similarity to known kinesins having such activity. It is also an object to provide methods of use of the compounds provided herein, including methods of diagnosis, treatment of disorders related to the nervous system, treatment of disorders related to fungal infections, bioagricultural, including crop protection, and veterinary applications, and methods of identifying binding agents and modulators of the compounds provided herein.

SUMMARY OF THE INVENTION

The present invention provides for the first time TL-$\gamma$, an ATP-dependent, plus end-directed microtubule motor protein that is a member of the unc-104 family and the kinesin superfamily. Previously, the unc-104 family was not thought to exist in fungi. However, the present invention surprisingly provides identification and cloning of a nucleic acid encoding TL-$\gamma$ from a hyphal fungus.

In one aspect, the invention provides an isolated nucleic acid sequence encoding a kinesin superfamily, plus end-directed microtubule motor protein, wherein the motor protein has the following properties: (i) the protein's activity includes plus end-directed microtubule motor activity; and (ii) the protein has a tail domain that has greater than 60% amino acid sequence identity to a TL-$\gamma$ tail domain as measured using a sequence comparison algorithm.

In one embodiment, the protein further specifically binds to polyclonal antibodies raised against TL-$\gamma$ of SEQ ID NO:1.

In one embodiment, the nucleic acid encodes TL-$\gamma$. In another embodiment, the nucleic acid encodes SEQ ID NO: 1. In another embodiment, the nucleic acid has a nucleotide sequence of SEQ ID NO:2.

In one embodiment, the sequence comparison algorithm is PILEUP.

In one embodiment, the nucleic acid is amplified by primers that selectively hybridize under stringent hybridization conditions to the same sequence as the primer set: 5' ATGTCGGGCGGTGGAAATATC 3' (SEQ ID NO:3) and 5' GAATTCCTGCTTCGCTTTCA 3'(SEQ ID NO:4). In another embodiment, the nucleic acid selectively hybridizes under stringent hybridization conditions to SEQ ID NO:2.

In one embodiment, the nucleic acid has identity to a TL-$\gamma$ derived from a hyphal fungi. In another embodiment, the nucleic acid has identity to the TL-$\gamma$ derived from *Thermomyces lanuginosus*.

In another aspect, the invention provides an expression vector comprising a nucleic acid encoding a kinesin superfamily, plus end-directed microtubule motor protein, wherein the motor protein has one or more of the properties described above.

In one embodiment, the invention provides a host cell transfected with the vector.

In another aspect, the invention provides an isolated kinesin superfamily, plus end-directed microtubule motor protein, wherein the protein has one or more of the properties described above.

In one embodiment, the protein specifically binds to polyclonal antibodies generated against a tail, motor, or stalk domain of TL-$\gamma$. In another embodiment, the protein comprises an amino acid sequence of a TL-γ motor domain of SEQ ID NO:1.

In another aspect, the invention provides an antibody that specifically binds to TL-γ.

In one embodiment, the antibody specifically binds to a tail, motor, or stalk domain of TL-γ.

In another embodiment, the invention further provides chimeric antibodies, humanized antibodies, and the nucleic acids encoding the antibodies provided herein.

In another aspect, the invention provides a method for diagnosing hyphal fungal infections by detecting the presence of TL-γ in a sample, the method comprising the steps of: (i) obtaining a biological sample; (ii) contacting the biological sample with a TL-γ specific reagent that selectively binds to TL-γ; and, (iii) detecting the level of TL-γ specific reagent that selectively associates with the sample.

In one embodiment, the TL-γ specific reagent is selected from the group consisting of: TL-γ specific antibodies, TL-γ specific oligonucleotide primers, and TL-γ nucleic acid probes. In another embodiment, the sample is from a plant or vertebrate, preferably a human. In another embodiment, the specific reagent is part of a gene or protein array.

In another aspect, the invention provides a method for screening for modulators of TL-γ, the method comprising the steps of: (i) contacting biologically active TL-γ with at least one candidate agent at a test and control concentration and detecting whether a change in TL-γ activity occurs between the test and control concentration, wherein a change indicates a modulator of TL-γ. In one embodiment, the activity is selected from the group consisting of plus-end directed microtubule motor activity, ATPase activity and binding activity.

In one embodiment, the method further comprises the step of isolating biologically active TL-γ from a cell sample. In another embodiment, the biologically active TL-γ is recombinant. In another embodiment, the biologically active TL-γ comprises a motor, stalk or tail domain having identity to a motor, stalk or tail domain of *Thermomyces lanuginosus* TL-γ. In another embodiment, the biologically active TL-γ comprises an amino acid sequence of a TL-γ motor domain of SEQ ID NO:1.

In another aspect, the invention provides a kit for screening for modulators of TL-γ, the kit comprising; (i) a container holding biologically active TL-γ; and (ii) instructions for assaying for TL-γ activity, wherein the TL-γ activity is plus end-directed microtubule motor activity, binding activity, or ATPase activity.

In another aspect, the invention provides, in a computer system, a method of screening for mutations of kinesin superfamily, plus end-directed microtubule motor protein genes, the method comprising the steps of: (i) receiving input of a first nucleic acid sequence encoding a plus end-directed microtubule motor protein having a nucleotide sequence of SEQ ID NO:2 and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In another aspect, the invention provides, in a computer system, a method for identifying a three-dimensional structure of kinesin superfamily, plus end-directed microtubule motor proteins, the method comprising the steps of: (i) receiving input of an amino acid sequence of at least 10 amino acids of a plus end-directed microtubule motor protein or a nucleotide sequence of at least 30 nucleotides of a gene encoding the motor protein, the protein having an amino acid sequence of SEQ ID NO:1 and conservatively modified versions thereof; and (ii) generating a three-dimensional structure of the protein encoded by the amino acid sequence.

In one aspect, the nucleic acid comprises a sequence which encodes an amino acid sequence which has one or more of the following characteristics:

greater than 60% sequence identity with SEQ ID NO:1, preferably greater than 70%, more preferably greater than 80%, more preferably greater than 90 or 95% or, in another embodiment, has 98 to 100% sequence identity with SEQ ID NO:1;

greater than 70% sequence identity with amino acids 1–357 of SEQ ID NO:1, more preferably greater than 80%, more preferably greater than 90 or 95% or, in another embodiment, has 98 to 100% sequence identity with amino acids 1–357 of SEQ ID NO:1;

greater than 60% sequence identity with amino acids 443–601 of SEQ ID NO:1, preferably greater than 70%, more preferably greater than 80%, more preferably greater than 90 or 95% or, in another embodiment, has 98 to 100% sequence identity with amino acids 443–601 of SEQ ID NO:1;

greater than 50 or 55% sequence identity with amino acids 602–784 of SEQ ID NO:1, preferably greater than 65%, more preferably greater than 70 or 80%, more preferably greater than 90 or 95% or, in another embodiment, has 98 to 100% sequence identity with amino acids 602–784 of SEQ ID NO:1.

In one embodiment, the nucleic acid comprises a sequence which has one or more of the following characteristics:

greater than 55 or 60% sequence identity with SEQ ID NO:2, preferably greater than 70%, more preferably greater than 80%, more preferably greater than 90 or 95% or, in another embodiment, has 98 to 100% sequence identity with SEQ ID NO:2;

greater than 65% sequence identity with nucleotides 1–1071 of SEQ ID NO:2, more preferably greater than 70 or 80%, more preferably greater than 90 or 95% or, in another embodiment, has 98 to 100% sequence identity with nucleotides 1–1071 of SEQ ID NO:2;

greater than 55%, preferably greater than 65%, more preferably greater than 70 or 80%, more preferably greater than 90 or 95% or, in another embodiment, has 98 to 100% sequence identity with nucleotides 1327–1803 of SEQ ID NO:2;

greater than 45 or 55%, preferably greater than 65%, more preferably greater than 70 or 80%, more preferably greater than 90 or 95% or, in another embodiment, has 98 to 100% sequence identity with nucleotides 1804–2352 of SEQ ID NO:2.

In another embodiment provided herein, the nucleic acid hybridizes under stringent conditions to a nucleic acid having a sequence or complementary sequence thereof selected from the group consisting of SEQ ID NO:2, nucleotides 1–1071 of SEQ ID NO:2, nucleotides 1327–1803 of SEQ ID NO:2, and 1804–2352 of SEQ ID NO:2.

In one aspect, the protein provided herein comprises an amino acid sequence which has one or more of the following characteristics:

greater than 60% sequence identity with SEQ ID NO:1, preferably greater than 70%, more preferably greater than 80%, more preferably greater than 90 or 95% or, in another embodiment, has 98 to 100% sequence identity with SEQ ID NO:1;

greater than 70% sequence identity with amino acids 1–357 of SEQ ID NO:1, more preferably greater than 80%, more preferably greater than 90 or 95% or, in another embodiment, has 98 to 100% sequence identity with amino acids 1–357 of SEQ ID NO:1;

greater than 60% sequence identity with amino acids 443–601 of SEQ ID NO: 1, preferably greater than 70%, more preferably greater than 80%, more preferably greater than 90 or 95% or, in another embodiment, has 98 to 100% sequence identity with amino acids 443–601 of SEQ ID NO:1;

greater than 50 or 55% sequence identity with amino acids 602–784 of SEQ ID NO:1, preferably greater than 65%, more preferably greater than 70 or 80%, more preferably greater than 90 or 95% or, in another embodiment, has 98 to 100% sequence identity with amino acids 602–784 of SEQ ID NO: 1.

BRIEF DESCRIPTION OF THE DRAWINGS

Not applicable.

DETAILED DESCRIPTION OF THE INVENTION

I. Introduction

The present invention provides for the first time a nucleic acid encoding TL-γ. This protein is a member of both the kinesin superfamily of motor proteins and the unc-104 motor protein family, having ATP-dependent, plus end-directed microtubule motor activity. The surprising discovery of TL-γ in hyphal fungi, but not non-hyphal fungi, indicates that this motor protein is likely involved in organelle transport, i.e., hyphal or axonal transport. The TL-γ nucleic acid and protein are therefore useful in a number of diagnostic, medicinal, veterinarial, bioagricultural, and research applications. Thus, included in this invention are methods for discriminating between hyphal and non-hyphal fungi and providing means of and compositions for diagnosing hyphal fungi infections. The invention also provides methods of assaying for modulators of TL-γ and fragments thereof as further defined herein. Such modulators include inhibitors which are useful for treating diseases caused by hyphal fungi. Such modulators are also useful for treating diseases caused by mutated TL-γ as further defined herein, such as neurodegenerative diseases involving anterograde axonal transport. Further diagnostic, medicinal, veterinarial, bioagricultural and research applications are described below.

In one aspect, TL-γ can be defined by having at least one or preferably more than one of the following functional and structural characterisitcs. Functionally, TL-γ has a plus-end directed microtubule motor activity that is ATP dependent (see, e.g., Example II, where ATP or another nucleotide triphosphate is included in the motility assay for motor activity). This activity is likely related to organelle transport such as in axons and hyphae. In one embodiment, recombinant TL-γ expressed in *E. coli* is thermo-resistant and unusually stable. For example, in one embodiment, TL-γ retains 100% activity from 0° C. to 40° C., with 70% activity at 45° C., 5% activity at 50° C., and 0% activity at 55° C. (as tested using a microtubule stimulated ATPase assay after incubation for 15 minutes at the test temperature). TL-γ activity can also be described in terms of its binding activity. For example, TL-γ is known to bind to microtubules, interact with hydrolyzable energy providing compounds, and compounds derived from the marine sponge Adocia. Other compounds which bind to TL-γ, such as antibodies, are further described below.

The novel nucleotides sequences provided herein encode TL-γ or fragments thereof. Thus, in one aspect, the nucleic acids provided herein are defined by the novel proteins provided herein. The protein provided herein comprises an amino acid sequence which has one or more of the following characteristics: greater than 60% sequence identity with SEQ ID NO:1, preferably greater than 70%, more preferably greater than 80%, more preferably greater than 90 or 95% or; in another embodiment, has 98 to 100% sequence identity with SEQ ID NO:1; greater than 70% sequence identity with amino acids 1–357 of SEQ ID NO:1, more preferably greater than 80%, more preferably greater than 90 or 95% or, in another embodiment, has 98 to 100% sequence identity with amino acids 1–357 of SEQ ID NO:1; greater than 60% sequence identity with amino acids 443–601 of SEQ ID NO:1, preferably greater than 70%, more preferably greater than 80%, more preferably greater than 90 or 95% or, in another embodiment, has 98 to 100% sequence identity with amino acids 443601 of SEQ ID NO:1; greater than 50 or 55% sequence identity with amino acids 602–784 of SEQ ID NO:1, preferably greater than 65%, more preferably greater than 70 or 80%, more preferably greater than 90 or 95% or, in another embodiment, has 98 to 100% sequence identity with amino acids 602–784 of SEQ ID NO:1. As described above, when describing the nucleotide is terms of the SEQ ID NO:2, the sequence identity may be slightly lower due to the degeneracy in the genetic code.

In one embodiment, the nucleotide sequence of TL-γ (SEQ ID NO:2) encodes a protein of approximately 784 amino acids with a predicted molecular weight of approximately 115 kDa and a predicted range of 105 kDa to 130 kDa. TL-γ is a member of the kinesin superfamily of motor proteins as evidenced by the sequence of its motor domain, and a member of the unc-104 motor family as evidenced by the sequence of its "stalk" domain. The predicted structure of TL-γ consists of an amino-terminal, kinesin-like microtubule "motor" domain (approximately amino acids 1–357 of TL-γ); a "neck" domain (approximately amino acids 358–442 of TL-γ) that links the motor to the "stalk" domain, which is the unc-104 family domain (approximately amino acids 443–601 of TL-γ; and a "tail" domain (approximately amino acids 602 to the C-terminal end of TL-γ). Within the stalk domain (residues 443–601) *Thermomyces lanuginosus* TL-γ and *C. elegans* unc-104 share 45% identity.

As defined by the sequence identity and/or hybridization characteristics described herein, the invention herein includes specific embodiments to polymorphic variants, alleles orthologs, and inter- and intra-species homologues of TL-γ. The present invention therefore also provide polymorphic variants of TL-γ: variant #1, in which an isoleucine residue is substituted for a valine residue at amino acid position 713; variant #2, in which a glutamic acid residue is substituted for an aspartic acid residue at amino acid position 762; and variant #3, in which a aspartic acid residue is substituted for a glutamic acid residue at amino acid position 774.

Portions of the TL-γ nucleotide sequence may be used to identify polymorphic variants, orthologs, alleles, and homologues of TL-γ, as well additional members of the unc-104 family of motor proteins in hyphal fungi. This identification can be made in vitro, e.g., under stringent hybridization conditions and sequencing, or by using the sequence information in a computer system for comparison with other nucleotide sequences. Typically, identification of polymorphic variants, orthologs, alleles, and homologues of TL-γ is made by comparing the amino acid sequence of the tail domain (approximately amino acids 602 to the C-terminal end of TL-γ). Amino acid identity of approximately 50% or above, preferable 60% or above, in the tail domain typically is one characteristic that demonstrates that a protein is a TL-γ. Similarly, the percent identity of the stalk domain is used to determine membership in the unc-104 motor protein family (approximately amino acids 443–601 of TL-γ). Amino acid identity of approximately 40% or above in the stalk domain typically demonstrates a protein is a member of the unc-104 family. Sequence comparison can be performed using any of the sequence comparison algorithms discussed below, with PILEUP as a preferred algorithm.

The activity of any of the peptides provided herein can be routinely confirmed by the assays provided herein such as those which assay microtubule motility, ATPase activity or binding activity. In one embodiment, polymorphic variants, alleles, and orthologs, homologues of TL-γ are confirmed by using the microtubule motility assay described in Example II. This assay is typically used to demonstrate that a protein having about 50% or greater, preferably 60% or greater amino acid identity to the "tail" region of TL-γ shares the same functional characteristics as TL-γ and is therefore a species of TL-γ. Typically, *Thermomyces lanuginosus* TL-γ is used as a positive control in comparison to the putative TL-γ protein to demonstrate the identification of a polymorphic variant, ortholog, allele, or homologue of TL-γ.

TL-γ nucleotide sequence information may also be used to construct models of the motor protein in a computer system. These models are subsequently used to identify compounds that can modulate TL-γ or kinesin superfamily protein function.

In one embodiment, TL-γ is found in *Thermomyces lanuginosus*, a hyphal fungus, and is predicted to exist in other hyphal fungi such as Aspergillus and Neurospora. However, TL-γ is absent in non- or pseudo- hyphal fungi such as Candida and Saccharomyces.

The isolation of biologically active TL-γ for the first time provides a means for assaying for modulators of this kinesin superfamily protein. Biologically active TL-γ is useful for identifying modulators of TL-γ or fragments thereof, unc-104 family members, and kinesin superfamily members using in vitro assays such as microtubule gliding assays (see, e.g., Example II), ATPase assays (Kodama et al., *J. Biochem.* 99:1465–1472 (1986); Stewart et al., *Proc. Nat'l Acad. Sci. USA* 90:5209–5213 (1993)), and binding assays including microtubule binding assays (Vale et al., *Cell* 42:39–50 (1985)). In vivo assays and uses are provided herein as well. Such modulators identified using biologically active TL-γ can be used therapeutically to treat infections of hyphal fungi and neurodegenerative diseases involving defective anterograde neuronal transport. Also provided herein are methods of identifying candidate agents which bind to TL-γ and portions thereof.

TL-γ also provides a convenient diagnostic marker for hyphal fungi, e.g., antibodies or other probes for TL-γ can be used in vitro to discriminate between hyphal fungi and non-hyphal fungi infections, e.g., between Candida and Aspergillus infections.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, bioagricultural and research based applications.

II. Definitions

As used herein, the following terms have the meanings ascribed to them unless specified otherwise.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated TL-γ nucleic acid is separated from open reading frames that flank the TL-γ gene and encode proteins other than TL-γ. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. Unless specifically limited, the term encompasses nucleic acids containing known analogues of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

A "label" is a composition detectable by spectroscopic, photochemical, biochemical, immunochemical, or chemical means. For example, useful labels include fluorescent proteins such as green, yellow, red or blue fluorescent proteins, $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radio-label into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe.

"Amplification" primers are oligonucleotides comprising either natural or analogue nucleotides that can serve as the basis for the amplification of a select nucleic acid sequence. They include, e.g., polymerase chain reaction primers and ligase chain reaction oligonucleotides.

The term "recombinant" when used with reference, e.g., to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "identical" in the context of two nucleic acids or polypeptide sequences refers to the residues in the two sequences that are the same when aligned for maximum correspondence, as measured using one of the following "sequence comparison algorithms."

The phrase "substantially identical" in the context of two nucleic acids or polypeptides refers to the residues in the two sequences that have at least 50%, preferably 60%, 70%, 80%, 90% or higher identity when aligned for maximum correspondence over a domain of the protein, e.g., the stalk, motor, or tail domain of T1-γ, or other regions defined herein, as measured using one of the following algorithms. Optimal alignment of sequences for comparison can be conducted, e.g., by the local homology algorithm of Smith & Waterman, *Adv. Appl. Mach.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison, e.g., the tail, motor, or stalk domains of TL-γ. In one example, TL-γ was compared to other kinesin superfamily sequences (e.g., Kif1A, Kif1B and unc-104) using the following parameters: default gap weight (3.00), default gap length weight (0.10), and weighted end gaps. The resulting dendogram placed TL-γ in one cluster, with unc-104, Kif1B and Kif1A in the next most closely related cluster.

Another example of algorithm that is suitable for determining sequence similarity is the BLAST algorithm, which is described in Altschul et al., *J. Mol. Biol.* 215:403–410 (1990). Software for performing BLAST analyses is publicly available through the National Center for Biotechnology Information (http:/lwww.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=4, and a comparison of both strands.

The BLAST algorithm performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to an TL-γ nucleic acid if the smallest sum probability in a comparison of the test nucleic acid to an TL-γ nucleic acid is less than about 0.1, more preferably less than about 0.01, and most preferably less than about 0.001. Where the test nucleic acid encodes a TL-γ polypeptide, it is considered similar to a specified TL-γ nucleic acid if the comparison results in a smallest sum probability of less than about 0.5, and more preferably less than about 0.2.

The phrase "substantially identical" in the context of two nucleic acids or polypeptides thus typically means that a polynucleotide or polypeptide comprises a sequence that has at least about 50% identity, preferably at least about 60–80% sequence identity, and most most preferably at least about 90–95%, compared to a reference sequence using the programs described above (preferably PILEUP) using standard parameters. One indication that two nucleic acid sequences or polypeptide are substantially identical is that the polypeptide which the first nucleic acid encodes is immunologically cross reactive with the polypeptide encoded by the second nucleic acid. Thus, a polypeptide is substantially identical to a second polypeptide, for example, where the two peptides differ only by a conservative substitution. Another indication that two nucleic acid sequences are substantially identical is that the two molecules hybridize to each other under stringent conditions.

The phrase "selectively hybridizes tow refers to the binding, duplexing, or hybridizing of a molecule only to a particular nucleotide sequence under stringent hybridization conditions when that sequence is present in a complex mixture (e.g., total cellular) DNA or RNA. The phrase "stringent hybridization conditions" refers to conditions under which a probe will hybridize to its target subsequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents as formamide. Examplary stringent hybridization conditions include: 50% formamide, 5×SSC and 1% SDS, incubating at 42° C., or 5×SSC, 1% SDS, incubating at 65° C., with a wash in 0.2×SSC and 0. 1% SDS at 65° C.

The phrase "a sequence encoding a gene product" refers to a nucleic acid that contains sequence information, e.g., for a structural RNA such as rRNA, a tRNA, the primary amino acid sequence of a specific protein or peptide, a binding site for a trans-acting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

"Antibody" refers to a polypeptide substantially encoded by an immunoglobulin gene or immunoglobulin genes, or fragments thereof which specifically bind and recognize an antigen. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

An "anti-TL-γ" antibody is an antibody or antibody fragment that specifically binds a polypeptide encoded by the TL-γ gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Humanized antibodies" refer to forms of non-human (e.g., murine) antibodies which are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulin (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature, 332:323–329 (1988); and Presta, Curr. Op. Struct. Biol., 2:593–596 (1992)).

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to TL-γ with the amino acid sequence encoded in SEQ ID NO:1 can be selected to obtain only those antibodies that are specifically immunoreactive with TL-γ and not with other proteins, except for polymorphic variants, orthologs, alleles, and closely related homologues of TL-γ. This selection may be achieved by subtracting out antibodies that cross react with molecules such as *C. elegans* unc-104 and mammalian Kif1. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as plant cells, CHO, HeLa and the like. Both primary cells and tissue cultures cells are included in this definition.

"Biological sample" as used herein is a sample of biological tissue or fluid that contains TL-γ or nucleic acid encoding TL-γ protein. Such samples include, but are not limited to, tissue isolated from hyphal fungi or tissue suspected of being infected with hyphal fungi. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

The term "in vivo" refers to applications which occur in a cell while in an organism. The term "in vitro" refers to applications which are outside of the organism, and can be in a cell or cell free environment. "In situ" refers to applications which undergo a combination of environments, for example, when a cell is manipulated and then transposed to an organism.

A "therapeutic", or the phrase "medicinal or veterinary uses" as used herein refers to a compound which is believed to be capable of modulating TL-γ activity which can have application in both human and animal disease. Such modulators would be desirable in a number of conditions including but not limited to: neurodegenerative diseases including Alzheimer's Disease, Parkinson's Disease, Huntington's Disease, Frontotemporal Dementias, Amyotrophic Lateral Sclerosis and fungal diseases such as aspergillosis, histoplasmosis, coccidiodomycosis and blastomycosis.

A "diagnostic" as used herein is a compound that assists in the identification and characterization of a health or disease state, including identification of the presence or absence of the nucleic acids and peptides provided herein. The diagnostic can be used in any cell, including plant or animal cells, using standard assays as is known in the art.

"Bioagricultural" as used herein refers to applications or a chemical or biological compound that has utility in agriculture and functions to foster food or fiber crop protection or yield improvement. For example, one such compound may serve as a fungicide to control the spreading of plant diseases.

"High throughput screening" as used herein refers to an assay which provides for multiple candidate agents or samples to be screened simultaneously. As further described below, examples of such assays may include the use of microtiter plates by and nucleic acid or protein arrays which are especially convenient because a large number of assays can be carried out simultaneously, using small amounts of reagents and samples.

"Candidate agent" encompasses numerous chemical classes of compounds and is further defined below. Embodiments include organic molecules, preferably small organic compounds having a molecular weight of more than 100 and less than about 2,500 daltons. In one embodiment, the candidate agent is selected from the group consisting of small organic molecules, oligonucleotides, peptides and antibodies".

The phrase "plus end-directed microtubule motor activity" refers to the activity of a motor protein such as TL-γ to power movement toward the "plus" ends of microtubules. Microtubules are conventionally referred to as having plus (fast growing) and minus ends (slow growing). This phrase includes polypeptides that are larger or smaller than TL-γ or its motor domain, providing that the polypeptide retains the plus end-directed activity.

The phrase "motor domain" refers to the domain of TL-γ that confers the plus end-directed microtubule motor activity on the protein (approximately amino acids 1–357 of TL-γ) and confers membership in the kinesin superfamily of motor proteins through a sequence identity of approximately 35–45% identity to the motor domain of true kinesin.

The phrase "stalk domain" refers to the domain of TL-γ that confers membership in the unc-104 family of motor proteins (approximately amino acids 443–601 of TL-γ). This domain can be used to identify other members of the unc-104 family, particularly in other hyphal fungi, through amino acid sequence identity comparison using a sequence comparison algorithm such as PILEUP. Typically, members of the unc-104 family share at least about 40% amino acid identity at the stalk domain.

The phrase "tail domain" refers to the domain of TL-γ that can be used to identify this particular protein (approximately amino acids 602 to the C-terminal end of TL-γ). This domain can be used to identify TL-γ polymorphic variants, TL-γ alleles orthologs, and homologues of TL-γ, through amino acid sequence identity comparison using a sequence comparison algorithm such as PILEUP.

"TL-γ" refers to a plus end-directed microtubule motor protein found in hyphal fungi, which is a member of the kinesin superfamily of microtubule motor proteins and a member of the unc-104 family of motor proteins. TL-γ has activity such as ATPase activity, binding activity and plus end-directed microtubule motor activity. The term TL-γ therefore refers to polymorphic variants, alleles, orthologs, mutants, and closely related variants that have a tail domain that has greater than about 50% amino acid sequence identity, preferably about 60% amino acid sequence identity, to a TL-γ tail domain. In addition, such polymorphic variants, orthologs, alleles, mutants, and closely related variants typically bind to polyclonal antibodies raised against SEQ ID NO:1, or antibodies raised against the tail domain of SEQ ID NO:1.

"Modulators," "inhibitors," and "activators of TL-γ" refer to modulatory molecules identified using in vitro and in vivo assays for TL-γ activity. Such assays include ATPase activity, microtubule gliding, microtubule depolymerizing activity, and binding activity such as microtubule binding activity. Samples or assays that are treated with a candidate agent at a test and control concentration. The control concentration can be zero. If there is a change in TL-γ activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Biologically active" TL-γ refers to TL-γ that has ATPase and plus end directed microtubule motor activity, as tested, e.g., in an ATPase assay, a microtubule gliding assay, or a microtubule binding assay. "ATPase activity" refers to the ability of TL-γ to hydrolyze ATP.

"Hyphal fungi" refers to fungi that form or have the ability to form branched filaments that form a mycelium. Examples of hyphal fungi include Aspergillus, Neurospora, Arabidopsis, and Thermomyces. Examples of non-hyphal or pseudo-hyphal fungi include Candida, Schizosaccharomyces, and Saccharomyces, which exist as single cells that reproduce by budding or division (see, e g., Webster, *Introduction to Fungi* (1970)).

"*Thermomyces lanuginosus*" is a thermophilic, hyphal fungi.

III. Isolation of the gene encoding TL-γ

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding TL-γ

In general, the nucleic acid sequences encoding TL-γ and related nucleic acid sequence homologues are cloned from cDNA and genomic DNA libraries or isolated using amplification techniques with oligonucleotide primers. For example, TL-γ sequences can be isolated from *Thermomyces lanuginosus* nucleic acid (genomic or cDNA) libraries by hybridizing with a nucleic acid probe, the sequence of which can be derived from SEQ ID NO:2, preferably from the tail domain.

Amplification techniques using primers can also be used to amplify and isolate TL-γ from DNA or RNA. The following primers can also be used to amplify a sequence of TL-γ: 5' ATGTCGGGCGGTGGAAATATC 3'(SEQ ID NO:3) and 5' GAATTCCTGCTTCGCTGTTTTCA 3' (SEQ ID NO:4). TL-γ can also be amplified using degenerate oligonucleotide primers (see Example I). These primers can be used, e.g., to amplify a probe of several hundred nucleotides, which is then used to screen a library for full-length TL-γ. Alternatively, the nucleic acid for TL-γ can be directly amplified.

Nucleic acids encoding TL-γ can also be isolated from expression libraries using antibodies as probes. Such polyclonal or monoclonal antibodies can be raised using the sequence of SEQ ID NO:1.

TL-γ polymorphic variants, orthologs, alleles, and homologues that are substantially identical to TL-γ can be isolated using TL-γ nucleic acid probes and oligonucleotides derived e.g., from SEQ ID NO:2, under stringent hybridization conditions, by screening libraries. Alternatively, expression libraries can be used to clone TL-γ and TL-γ polymorphic variants, orthologs, alleles, and homologues, by detecting expressed homologues immunologically with antisera or purified antibodies made against TL-γ that also recognize and selectively bind to the TL-γ homologue.

Appropriate primers and probes for identifying the gene encoding TL-γ in other species such as other hyphal fungi and organisms listed herein such as animals and humans are generated from comparisons of the sequences provided herein (SEQ ID NOS: 1 and 2 and polymorphic variants #1–3). As described above, antibodies can be used to identify TL-γ homologues. For example, antibodies made to the motor domain of TL-γ, the tail domain of TL-γ, the stalk domain of Tl-γ, or to the whole protein are useful for identifying TL-γ homologues. For identification of other unc-104 family members in hyphal fungi, preferably the stalk region is used to generate primers and probes.

To make a cDNA library, one should choose a source that is rich in the mRNA of choice, e.g., TL-γ. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffmnan, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating TL-γ nucleic acid and its homologues combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of TL-γ directly from mRNA, from cDNA, from genomic libraries or cDNA libraries. Degenerate oligonucleotides can be designed to amplify TL-γ homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of TL-γ encoding mRNA in physiological samples, for nucleic acid sequencing, or for other purposes. Genes amplified by the PCR reaction can be purified from agarose gels and cloned into an appropriate vector.

Gene expression of TL-γ can also be analyzed by techniques known in the art, e.g., reverse transcription and amplification of mRNA, isolation of total RNA or poly A+RNA, northern blotting, dot blotting, in situ hybridization, RNase protection and the like.

Synthetic oligonucleotides can be used to construct recombinant TL-γ genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the TL-γ gene. The specific subsequence is then ligated into an expression vector.

The gene for TL-γ is typically cloned into intermediate vectors before transformation into prokaryotic or eukaryotic cells for replication and/or expression. These intermediate vectors are typically prokaryote vectors or shuttle vectors.

C. Expression in Prokaryotes and Eukaryotes

To obtain high level expression of a cloned gene, such as those cDNAs encoding TL-γ, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the TL-γ protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. The pET23 expression system (Novagen) is a preferred prokaryotic expression system.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the TL-γ encoding nucleic acid in host cells. A typical expression cassette thus contains a promoter operably linked to the nucleic acid sequence encoding TL-γ and signals required for efficient polyadenylation of the transcript, ribosome binding sites, and translation termination. The nucleic acid sequence encoding TL-γ may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary rumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a TL-γ encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of TL-γ protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher ed., 1990)). Transformation of eukaryotic and prokaryotic cells are performed according to standard techniques (see, e.g., Morrison, *J. Bact.*, 132:349–351 (1977); Clark-Curtiss & Curtiss, *Methods in Enzymology*, 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing TL-γ.

After the expression vector is introduced into the cells, the transfected cells are cultured under conditions favoring expression of TL-γ, which is recovered from the culture using standard techniques identified below.

IV. Purification of TL-γ

Either naturally occurring or recombinant TL-γ can be purified for use in functional assays. Naturally occurring TL-γ is purified, e.g., from Thermomyces and any other source of a TL-γ homologue, such as other animals, plants, hyphal fungi (Aspergillus, etc.). Recombinant TL-γ is purified from any suitable expression system.

TL-γ may be purified to substantial purity by standard techniques, including selective precipitation with such substances as ammonium sulfate; column chromatography, immunopurification methods, and others (see, e.g., *Scopes, Protein Purification: Principles and Practice* (1982); U.S. Pat. No. 4,673,641; Ausubel et al., supra; and Sambrook et al., supra).

A number of procedures can be employed when recombinant TL-γ is being purified. For example, proteins having established molecular adhesion properties can be reversibly fused to TL-γ. With the appropriate ligand, TL-γ can be selectively adsorbed to a purification column and then freed from the column in a relatively pure form. The fused protein is then removed by enzymatic activity. Finally TL-γ could be purified using immunoaffinity columns. A preferred purification column is an Ni-NTA column.

A. Purification of TL-γ from Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of TL-γ inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension is typically lysed using 2–3 passages through a French Press. The cell suspension can also be homogenized using a Polytron (Brinkyman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. TL-γ is separated from other bacterial proteins by standard separation techniques, e.g., with Ni-NTA agarose resin.

Alternatively, it is possible to purify TL-γ from bacteria periplasm. After lysis of the bacteria, when TL-γ is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO$_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying TL-γ

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of TL-γ can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatoragphy

TL-γ can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of TL-γ

In addition to the detection of TL-γ genes and gene expression using nucleic acid hybridization technology, one can also use immunoassays to detect TL-γ. Immunoassays can be used to qualitatively or quantitatively analyze TL-γ. A general overview of the applicable technology can be found in Harlow & Lane, *Antibodies: A Laboratory Manual* (1988).

A. Antibodies to TL-γ

Methods of producing polyclonal and monoclonal antibodies that react specifically with TL-γ are known to those of skill in the art (see, e.g., Coligan, *Current Protocols in Immunology* (1991); Harlow & Lane, supra; Goding, *Monoclonal Antibodies: Principles and Practice* (2d ed. 1986); and Kobler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of TL-γ comprising immunogens may be used to produce antibodies specifically reactive with TL-γ. For example, recombinant TL-γ or a antigenic fragment thereof such as the motor, stalk, or tail domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to TL-γ. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-TL-γ proteins or even other homologous proteins from other organisms (e.g., *C. elegans* unc-104 or mammalian Kif1), using a competitive binding immunoassay. Specific polyclonal antisera and monoclonal antibodies will usually bind with a $K_D$ of at least about 0.1 mM, more usually at least about 1 μM, preferably at least about 0.1 μM or better, and most preferably, 0.01 μM or better.

Once TL-γ specific antibodies are available, TL-γ can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio ed., 1980); and Harlow & Lane, supra.

As indicated above, another application of antibodies herein is for therapeutic purposes, thus, humanized antibodies are also provided herein. In a preferred method, the humanized antibody is formulated so as to be taken up by the cell. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom & Winter, *J. Mol. Biol.*, 227:381 (1991); Marks et al., *J. Mol. Biol.*, 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., *J. Immunol.*, 147(1):86–95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779–783 (1992); Lonberg et al., *Nature* 368:856–859 (1994); Morrison, *Nature* 368:812–13 (1994); Fishwild et al., *Nature* Biotechnology 14:845–51 (1996); Neuberger, *Nature Biotechnology* 14:826 (1996); Lonberg and Huszar, *Intern. Rev. Immunol.* 13:65–93 (1995).

The antibodies provided herein can also be bispecific in one embodiment. Bispecific antibodies are monoclonal, preferably human or humanized, antibodies that have binding specificities for at least two different antigens. In the present case, one of the binding specificities is for the TL-γ or a portion thereof, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. It is contemplated that the antibodies may be prepared in vitro using known methods in synthetic protein chemistry, including those involving crosslinking agents.

B. Binding Assays

As explained above, TL-γ is found in hyphal fungi, but not in non-hyphal fungi. Thus, TL-γ provides a marker with which to discriminate between these two types of fungi. Additionally, as described above, antibodies can be used for treatment or to identify the presence of TL-γ having the sequence identity characteristics as described herein. Additionally, antibodies can be used to identify modulators of the interaction between the antibody and TL-γ as further described below. While the following discussion is directed toward the use of antibodies in the use of binding assays, it is understood that the same general assay formats such as those described for "non-competitive" or "competitive" assays can be used with any compound which binds to TL-γ such as microtubules or the compounds described in Ser. No. 60/070,772.

In a preferred embodiment, TL-γ is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the TL-γ or antigenic subsequence thereof). The antibody (e.g., anti-TL-γ) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled TL-γ polypeptide or a labeled anti-TL-γ antibody. Alternatively, the labeling agent may be a third moiety, such a secondary antibody, that specifically binds to the antibody/TL-γ complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting TL-γ in samples may be either competitive or noncompetitive. Noncompetitive immunoassays are assays in which the amount of antigen is directly measured. In one preferred "sandwich" assay, for example, the anti-TL-γ antibodies can be bound directly to a solid substrate on which they are immobilized. These immobilized antibodies then capture TL-γ present in the test sample. TL-γ is thus immobilized is then bound by a labeling agent, such as a second TL-γ antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive assay formats

In competitive assays, the amount of TL-γ present in the sample is measured indirectly by measuring the amount of a known, added (exogenous) TL-γ displaced (competed away) from an anti-TL-γ antibody by the unknown TL-γ present in a sample. In one competitive assay, a known amount of TL-γ is added to a sample and the sample is then contacted with an antibody that specifically binds to TL-γ. The amount of exogenous TL-γ bound to the antibody is inversely proportional to the concentration of TL-γ present in the sample. In a particularly preferred embodiment, the antibody is immobilized on a solid substrate. The amount of TL-γ bound to the antibody may be determined either by measuring the amount of TL-γ present in a TL-γ/antibody complex, or alternatively by measuring the amount of remaining uncomplexed protein. The amount of TL-γ may be detected by providing a labeled TL-γ molecule.

A hapten inhibition assay is another preferred competitive assay. In this assay the known TL-γ is immobilized on a solid substrate. A known amount of anti-TL-γ antibody is added to the sample, and the sample is then contacted with the immobilized TL-γ. The amount of anti-TL-γ antibody bound to the known immobilized TL-γ is inversely proportional to the amount of TL-γ present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity determinations

Immunoassays in the competitive binding format can also be used for crossreactivity determinations. For example, a protein at least partially encoded by SEQ ID NO:1 can be immobilized to a solid support. Proteins (e.g., *C. elegans* unc-104 or mammalian Kif1) are added to the assay that compete for binding of the antisera to the immobilized antigen. The ability of the added proteins to compete for binding of the antisera to the immobilized protein is compared to the ability of TL-γ encoded by SEQ ID NO:1 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues.

The imnmunoabsorbed and pooled antisera are then used in a competitive binding immununoassay as described above to compare a second protein, thought to be perhaps the protein of this invention, to the immunogen protein (i.e., TL-γ of SEQ ID NO:1). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:1 that is required to inhibit 50% of binding, then the second protein is said to specifically bind to the polyclonal antibodies generated to a TL-γ immunogen.

Other assay formats

Western blot (immunoblot) analysis is used to detect and quantify the presence of TL-γ in the sample. The technique generally comprises separating sample proteins by gel electrophoresis on the basis of molecular weight, transferring the separated proteins to a suitable solid support, (such as a nitrocellulose filter, a nylon. filter, or derivatized nylon filter), and incubating the sample with the antibodies that specifically bind TL-γ. The anti-TL-γ antibodies specifically bind to the TL-γ on the solid support. These antibodies may be directly labeled or alternatively may be subsequently detected using labeled antibodies (e.g., labeled sheep antimouse antibodies) that specifically bind to the anti-TL-γ antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of non-specific binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound tothe molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize TL-γ, or secondary antibodies that recognize anti-TL-γ.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemilaminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of TL-γ

TL-γ and its homologues are plus end-directed microtubule motors. The activity of TL-γ can be assessed using a variety of in vitro or in vivo assays, e.g., microtubule gliding assays (see Example II), binding assasys such as microtubule binding assays, microtubule depolymerization assays, and ATPase assays (Kodama et al., *J. Biochem.* 99: 1465–1472 (1986); Stewart et al., *Proc. Nat'l Acad. Sci. USA* 90: 5209–30 5213 (1993); (Lombillo et al., *J. Cell Biol.* 128:107–115 (1995); (Vale et al., *Cell* 42:39–50 (1985)). A preferred assay for high throughput screening is an ATPase assay with colorimetric detection, e.g., malachite green for end-point detection or coupled PK/LDH for continuous rate monitoring.

Such assays can be used to test for the activity of Tl-γ isolated from endogenous sources or recombinant sources. Furthermore, such assays can be used to test for modulators of TL-γ. Modulators of TL-γ, particularly inhibitors, can be used to control hyphal fungi infections, and modulators of Tl-γ can be used to treat neurodegenerative diseases involving members of the unc-104 family of motor proteins, including conditions including but not limited to: neurodegenerative diseases including Alzheimer's Disease, Parkinson's Disease, Huntington's Disease, Frontotemporal Dementias, and Amyotrophic Lateral Sclerosis. Modulators of TL-γ are useful as pharmaceutical treatments for hyphal fungi infections of mammals, particularly humans, such as histoplasmosis (*Histoplasma capsulatum*), coccidiodomycosis (*Coccidioides immitis*), blastomycosis (*Blastomyces dermatitidis*), and aspergillosis (*Aspergillus fumigatus, A. flavus*, and *A. niger*). Such infections are particularly found in immunocompromised patients such as HIV-infected patients, cancer patients, and transplant patients.

Modulators of TL-γ activity are tested using biologically active TL-γ e.g., thermostable *Thermomyces lanuginosus* TL-γ. Modulation is tested using one of the in vitro or in vivo assays described herein, e.g., ATPase, microtubule gliding, and microtubule binding.

In specific embodiments, screens may be designed to first find candidate agents that can bind to TL-γ (also referred to as TL gamma herein) proteins, and then these agents, and agents already known to bind to TL gamma may be used in assays that evaluate the ability of the candidate agent to modulate TL gamma activity. Thus, as will be appreciated by those in the art, there are a number of different assays which may be run; binding assays and activity assays.

Thus, in a preferred embodiment, the methods comprise combining a TL gamma protein and a candidate agent, and determining the binding of the candidate agent to the TL gamma protein. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening against TL gamma. Particularly preferred in this embodiment are libraries of bacterial, fungal, viral, plant and mammalian proteins, with the latter being preferred, and human proteins being especially preferred.

In a preferred embodiment, the candidate agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach*), and peptide nucleic acid backbones and linkages (see Egholm, *J. Am. Chem. Soc.* 114:1895 (1992); Meier et al., *Chem. Int. Ed. Engl.* 31:1008 (1992);, Nielsen, *Nature,* 365:566 (1993); Carlsson et al., *Nature* 380:207 (1996)). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Eds. Sanghui and Cook; Mesmaeker et al., *Bioorganic & Medicinal Chem. Lett.* 4:395 (1994); Jeffs et al., *J. Biomolecular* NMR 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Sanghui and Cook. Nucleic acids containing one or more carbocyclic sugars are also included within the definition of nucleic acids (see Jenkins et al., *Chem. Soc. Rev.* (1995) pp. 169–176). Several nucleic acid analogs are described in Rawls, *C & E News,* Jun. 2, 1997 page 35. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate agents may be naturally occurring nucleic acids, random nucleic acids, or "biased" random nucleic acids. For example, digests of procaryotic or eukaryotic genomes may be used as is outlined above for proteins.

In a preferred embodiment, the candidate agents are organic chemical moieties, a wide variety of which are available in the literature.

The assays provided utilize TL gamma proteins as defined herein. In one embodiment, portions of TL gamma proteins are utilized; in a preferred embodiment, portions having TL gamma activity as described herein are used. In addition, the assays described herein may utilize either isolated TL gamma proteins or cells or animal models comprising the TL gamma proteins.

Generally, in a preferred embodiment of the methods herein, the TL gamma protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. In some embodiments, microtubules can be used. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used.

In a preferred embodiment, the TL gamma protein is bound to the support, and a candidate agent is added to the assay. Alternatively, the candidate agent is bound to the support and the TL gamma protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to the TL gamma protein may be done in a number of ways. In a preferred embodiment, the candidate agent is labeled, and binding determined directly. For example, this may be done by attaching all or a portion of the TL gamma protein to a solid support, adding a labeled candidate agent (for example a fluorescent label), washing off excess reagent, and determining whether the label is present on the solid support. Various blocking and washing steps may be utilized as is known in the art.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate agent is determined through the use of competitive binding assays as described in the preceding section, and is explicitly not limited to antibodies.

In a preferred embodiment, the methods comprise differential screening to identity agents that are capable of modulating the activity of the TL gamma proteins. In this embodiment, the methods comprise combining a TL gamma protein and a competitor in a first sample. A second sample comprises a candidate agent, a TL gamma protein and a competitor. The binding of the competitor is determined for both samples, and a change, or difference in binding between the two samples indicates the presence of an agent capable of binding to the TL gamma protein and thus modulating its activity. That is, if the binding of the competitor is different in the second sample relative to the first sample, the agent is capable of binding to the TL gamma protein. Activity can be measured and detected by other methods as described herein such as ATPase and motility assays.

Alternatively, a preferred embodiment utilizes differential screening to identify drug candidates that bind to the native TL gamma protein, but cannot bind to modified TL gamma proteins. The structure of the TL gamma protein may be modeled, and used in rational drug design to synthesize agents that interact with that site. Drug candidates that affect TL gamma bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

The proteins and nucleic acids provided herein can also be used for screening purposes wherein the protein-protein interactions of the TL gamma proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., *Nature* 340:245 (1989); Vasavada et al., *PNAS USA* 88:10686 (1991); Fearon et al., *PNAS USA* 89:7958 (1992); Dang et al., *Mol. Cell. Biol.* 11:954 (1991); Chien et al., *PNAS USA* 88:9578 (1991); and U.S. Pat. Nos. 5,283,173, 5,667,973, 5,468,614, 5,525,490, and 5,637,463.

In general, two nucleic acids are transformed into a cell, where one is a "bait" such as the gene encoding TL gamma or a portion thereof, and the other encodes a test candidate. Only if the two expression products bind to one another will an indicator, such as a fluorescent protein, be expressed. Using the same system and the identified TL gamma proteins the reverse can be performed. Namely, the TL gamma proteins provided herein can be used to identify new baits, or agents which interact with TL gamma proteins. Additionally, the two-hybrid system can be used wherein a test candidate is added in addition to the bait and the TL gamma protein encoding nucleic acids to determine agents which interfere with the bait and the TL gamma protein.

Yet another assay for compounds that modulate TL-γ activity involves computer assisted drug design, in which a computer system is used to generate a three-dimensional structure of TL-γ based on the structural information encoded by the amino acid sequence. The amino acid sequence interacts directly and actively with a preestablished algorithm in a computer program to yield secondary, tertiary, and quaternary structural models of the protein. The models of the protein structure are then examined to identify regions of the structure that have the ability to bind to ligands.

These regions are then used to identify ligands that bind to the protein. The three-dimensional structural model of the protein is generated by inputting channel protein amino acid sequences or nucleic acid sequences encoding a channel protein into the computer system. The amino acid sequence of the channel protein is selected from the group consisting of SEQ ID NO:1 and conservatively modified versions thereof. The amino acid sequence represents the primary sequence of the protein, which encodes the structural information of the protein. The at least 10 nucleotides of the amino acid sequence (or a nucleotide sequence encoding 10 amino acids) is input into the computer system from computer readable substrates that include, but are not limited to, electronic storage media (e.g., magnetic diskettes, tapes, cartridges, and chips), optical media (e.g., CD ROM, telephone lines), addresses to internet sites, and RAM. The three-dimensional structural model of the channel protein is then generated by the interaction of the amino acid sequence and the computer system. The software is commercially available programs such as Biopolymer, Quanta, and Insight.

The amino acid sequence represents a primary structure that encodes the information necessary to form the secondary, tertiary and quaternary structure of the protein. The software looks at certain parameters encoded by the primary sequence to generate the structural model. These parameters are referred to as "energy terms," and primarily include electrostatic potential, hydrophobic potential, solvent accessible surface, and hydrogen bonding. Secondary energy terms include van der Waals potential. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can input additional variables such as whether the protein is membrane bound or soluble, its location in the body, and whether it is cytoplasmic, surface, or nuclear. These variables along with the energy terms of the secondary structure are used to form the model of the tertiary structure. In modeling the tertiary structure, the computer program matches hydrophobic protein faces of secondary structure with like, and hydrophilic secondary structure with like.

Once the structure has been generated, potential ligand binding regions are identified by the computer system. Three-dimensional structures for potential ligands are generated by inputting amino acid and nucleotide sequences or chemical formulas of compounds, as described above. The three-dimensional structure of the potential ligand is then compared to that of the TL-γ protein to identify ligands that bind to TL-γ. Binding affinity between the protein and ligands is determined using energy terms to determine which ligands have an enhanced probability of binding to the protein.

Computer systems are also used to screen for mutations, polymorphic variants, orthologs, alleles and homologues of TL-γ genes, as well as for other members of the unc-104 motor protein family in hyphal fungi. Such mutations can be associated with disease states. Once the variants are identified, diagnostic assays can be used to identify patients having such mutated genes associated with disease states. Identification of the mutated TL-γ genes involves receiving input of a first nucleic acid sequence encoding a TL-γ an amino acid sequence selected from the group consisting of SEQ ID NO:1 and conservatively modified versions thereof. The sequence is input into the computer system as described above. The first nucleic acid sequence is then compared to a second nucleic acid sequence that has substantial identity to the first nucleic acid sequence. The second nucleic acid sequence is input into the computer system in the manner described above. Once the first and sequence sequences are compared, nucleotide differences between the sequences are identified. Such sequences can represent allelic differences in TL-γ genes, and mutations associated with disease states.

In this way, bioactive agents are identified. Compounds with pharmacological activity are able to enhance or interfere with the activity of the TL gamma protein. The compounds having the desired pharmacological activity may be administered in a physiologically acceptable carrier to a host, as previously described. The agents may be administered in a variety of ways, orally, parenterally e.g., subcutaneously, intraperitoneally, intravascularly; etc. Depending upon the manner of introduction, the compounds may be formulated in a variety of ways. The concentration of therapeutically active compound in the formulation may vary from about 0.1–100 wt. %. In the case of plants, sprays are a preferred embodiment.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In addition to the use of identifying modulators and the use in treatments and diagnostics, the nucleic acids provided herein can be used to provide cell and animal models. Moreover, the nucleic acids can be used in some cases to provide antisense molecules and transgenics. Examples of such include at least the following embodiments.

Nucleotide sequences encoding a TL gamma protein can also be used to construct hybridization probes for mapping the gene which encodes that TL gamma protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode TL gamma protein can also be used to generate either transgenic animals or "knock out" animals which, in turn, are useful in the development and screening of therapeutically useful reagents. A transgenic animal (e.g., a mouse, rat, sheep, cow) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a TL gamma protein can be used to clone genomic DNA encoding a TL gamma protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for the TL gamma protein transgene incorporation with tissue-specific enhancers. Transgenic animals that include a copy of a transgene encoding a TL gamma protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, homologues of the TL gamma protein can be used to construct a TL gamma protein "knock out" animal which has a defective or altered gene encoding a TL gamma protein as a result of homologous recombination between the endogenous gene encoding a TL gamma protein and altered genomic DNA encoding a TL gamma protein introduced into an embryonic cell of the animal. For example, cDNA encoding a TL gamma protein can be used to clone genomic DNA encoding a TL gamma protein in accordance with established techniques. A portion of the genomic DNA encoding a TL gamma protein can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, Cell 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., Cell 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (1987), pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TL gamma protein polypeptide.

It is understood that the models described herein can be varied. For example, "knock-in" models can be formed, or the models can be cell-based rather than animal models.

Nucleic acid encoding the TL gamma polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane (Zamecnik et at., *Proc. Natl. Acad. Sci. USA* 83:4143–4146 (19860). The oligonucleotides can be modified to enhance their uptake, e.g. by substituting their negatively charged phosphodiester groups by uncharged groups.

VII. Diagnostic Assays and Kits

As described above, TL-γ and its homologues are also a useful diagnostic tool in vitro for hyphal fungi infections and for discriminating between hyphal and non- or pseudo-hyphal fungi. Such assays use TL-γ specific reagents that specifically hybridize to TL-γ nucleic acid, such as TL-γ probes and primers, and TL-γ specific reagents that specifically bind to the TL-γ protein, e.g., TL-γ antibodies.

Nucleic acid assays for the presence of TL-γ DNA and RNA in a sample are useful diagnostic assays. Numerous techniques are known to those skilled in the art, including Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, TL-γ protein can be detected with the various immunoassay techniques described above. The test sample is typically compared to both a positive control (e.g, a sample from *Thermomyces lanuginosus* TL-γ or a sample expressing recombinant TL-γ) and a negative control (e.g., a negative sample from Saccharomyces).

The present invention also provides for kits for screening for modulators of Tl-γ. Such kits can be prepared from readily available materials and reagents. For example, such kits can comprise any one or more of the following materials: biologically active TL-γ, reaction tubes, and instructions for testing TL-γ activity. Preferably, the kit contains biologically active *Thermomyces lanuginosus* TL-γ. A wide variety of kits and components can be prepared according to the present invention, depending upon the intended user of the kit and the particular needs of the user. For example, the kit can be tailored for ATPase assays, microtubule gliding assays, or microtubule binding assays.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Cloning and Expression of TL-γ

A. Isolation of Nucleic Acid Encoding TL-γ and Expression Vector Constructs

Using PCR and degenerate primers, TL-γ was amplified from *Thermomyces lanuginosus* nucleic acid. The following primers were used for amplification: GCGCGGATCCATC/ TTTT/CGCC/T/ATAT/CGGT/C/A/GCAG/AAC (SEQ ID NO:5) (forward primer);

GCGCGAATTCTCA/G/TGAA/G/T/CCCA/G/TGCA/C/ GAG/AG/ATCA/G/T/CAC (SEQ ID NO:6) (reverse primer); and GCGCGAATTCTCA/G/TCTA/G/T/CCCA/G/TGCA/C/ GAG/AG/ATCA/G/T/CAC (SEQ ID NO:7) (reverse primer). The PCR reaction used total genomic DNA from *Thermomyces lanuginosus* as the initial tissue source for amplifying a portion of the motor domain of Tl-γ using the degenerate primers. This nucleic acid sequence was then used as a probe to isolate a longer TL-γ sequence. Both a library in lambda charon 4A (Nazar et al., *PNAS* 82:5608–5611 (1985) and a cDNA library (InVitrogen) were used for screening with the TL-γ probe to clone a full-length TL-γ sequence.

Clones of TL-γ were amplified with the degenerate primers using the following conditions: (1) 10 cycles of 1 minute at 94° C., 1.5 minutes at 30° C., and 1 minute at 72° C. followed by (2) 30 cycles of 1 minute at 94° C., 1 minute at 45° C., and minute at 72° C. The clones were sequenced according to standard techniques. The following hybridization conditions were used to screen the genomic and cDNA libraries, using a probe from amplification with degenerate primers: 65° C. overnight in 0.5 M sodium phosphate pH 7.2, 7% SDS, and 1 mM EDTA. The filter were washed 1 time for 15 minutes at 65° C. in 40 mM sodium phosphate pH 7.2, 4% SDS, and 1 mM EDTA and then three times at 65° C. in 40 mM sodium phosphate pH 7.2, 1% SDS, 1 mM EDTA The nucleotide and amino acid sequences of TL-γ are provided, respectively, in SEQ ID NO:2 and SEQ ID NO:1.

B. Expression and Purification of TL-γ

Recombinant TL-γ was prepared in order to test its activity in a microtubule gliding assay. Recombinant TL-γ was prepared using the pET23d expression sector, which is inducible in *E. coli* with IPTG.

First, TL-γ of SEQ ID NO:2 was cloned into the pET expression plasmid. The TL-γ nucleic acid was digested and ligated into pET23 (Novagen) to yield pET23-TL-γ in the following manner. First, the region of the motor and stalk domains were amplified using PCR from a cDNA clone using primers that introduced a NdeI restriction site at the predicted translation start site from TL-γ, and a HindIII restriction site at the 3' of this fragment. This fragment was inserted into the NdeI-HindIII sites of plasmid pET23b. Second, a HindIII-SacI fragment was excised from the genomic clone of TL-γ (this clone was previously subcloned in pBS-SK) and ligated into the HindIII-SacII sites of pET23b to give pET23b-TL-γ. The resulting plasmid encodes amino acids of 1–784 TL-γ. This plasmid includes a hexahistidine tag for protein purification.

This plasmid was transformed into *E. coli* strain BL21 (DE3). A culture inoculated with a single colony was grown at 37° C. in a modified LB medium (10 g bactotryptone, 5 g yeast extract, 5 g NaCl, 2 g MgSO$_4$, 1 g casaminoacids per liter, and 200 mg ampicillin per liter) to OD 600 of -1. The cultures were allowed to cool to room temperature and expression of fusion protein was induced with 0.5 mM IPTG at room temperature for 3–4 hours. After induction, the cells were typically used immediately to prepare TL-γ protein. However, cells can also be pelleted and stored at −80° C. or lower prior to protein isolation.

Cells were harvested by centrifugation approximately 4 hours after induction and resuspended in lysis buffer (50 mM Tris/HCl pH 7.5, 50 mM NaCl, 5 mM $MgCl_2$, 1 mM DTr, 1 mM PMSF, and 0.1 mM ATP), and lysed by 2–3 passages through a French press. Insoluble debris was removed by a centrifugation at 35,000 rpm in TI1270 rotor for 40 minutes at 4° C. Soluble protein in the supernatant was bound in batch to 0.5 ml of NI-NTA-agarose resin (Qiagen) for 15 minutes at 4° C. The resin was placed in a column and washed with 10–20 column volumes of PEM80 buffer (80 mM PIPES pH 6.9, 1 mM EGTA, and 1 mM $MgCl_2$) plus 10 mM imidazole. TL-γ protein recovered by elution with PEMBO containing 100 mM imnidazole. A typical yield was 1 mg per 1 L culture or approximately 1% of the total soluble protein. The protein was very stable, retaining 100% activity up to 40° C. after incubation for 15 minutes as measured using a microtubule dependent ATPase assay (see, e.g., Hackney et al., *J. Biol. Chem.* 264:15943–15948 (1989)). Freshly prepared protein was used to assay microtubule gliding activity, as described below.

Example II

Plus End-directed Microtubule Motor Activity

A. Preparation of Polarity Marked Microtubules and Motility Assay

Microtubule gliding assays were used to determine the activity of the recombinant TL-γ protein, e.g., whether it is a plus- or minus-end directed microtubule motor. The activity of TL-γ was tested, as follows.

Taxol stabilized microtubule seeds brightly labelled with rhodamine were prepared by incubating a 1:1 ratio of rhodamine labelled bovine brain tubulin (Hyman, et al., in *Methods in Enymology*, pp. 478–485 (Vallee, ed., 1992)) with unlabelled bovine brain tubulin at a final tubulin concentration of 2.5 mg/ml in PEM80 (80 mM Pipes pH 6.9, 1 mM EGTA, 1 mM $MgCl_2$) containing 10% glycerol, 1 μM taxol, 1 mM GTP at 37° C. for 15 minutes. This mixture was then diluted with 2.75 volumes of warm PEM80 containing 20 μM taxol and 2 mM GTP, and sheared by 5 passes through a Hamilton syringe.

Dimly rhodamine-labelled extensions were grown from the brightly labelled seeds in PEM80 containing 1 mM GTP and 1.5 mg/ml tubulin cocktail consisting of a mixture of N-ethyl maleimide modified tubulin (Hyman, et at., in *Methods in Enymology*, pp. 478–485 (Vallee, ed., 1992)), unlabelled tubulin and rhodamine labelled tubulin at a ratio of 0.1/0.52/0.38 for 30 minutes at 37° C. The resulting suspension of polarity marked microtubules was diluted with PEM80 containing 10 μM taxol and used to test motility.

25 μl flow chambers prepared from cover slips sealed with an Apiezon grease, were preadsorbed with TL-γ motor protein diluted to 0.1 mg/ml, and unbound protein removed by rinsing with 50 μl of PEM80. A microcubule/ATP mix consisting polarity marked microtubules in PEM80 containing 10 μM taxol, 2 mM MgATP, and an oxygen scavenging system (0.1 mg/ml catalase, 0.03 mg/ml glucose oxidase, 10 mM glucose, 0.1% β-mercaptoethanol (Kishino, et al., *Nature* 33:74–76 (1989)) was then flowed into the chamber.

Movement of microtubules was monitored at room temperature on a Zeiss Axioplan fluorescence microscope fitted with 63× Plan-Apochromat oil immersion objective, and a Princeton instruments cooled CCD. Automated time-lapse image acquisition and data analysis was performed using the MetaMorph software package (Universal Imaging, West Chester, Pa.).

B. TL-γ Activity

Recombinant TL-γ protein was attached a glass coverslip using non-specific adhesion and gliding of polarity marked microtubules containing brightly fluorescent rhodamine labelled seeds near their minus ends (Howard, et al., in *Motility Assays for Motor Proteins*, pp. 105–113 (Scholey, ed., 1993)) was recorded by time-lapse digital fluorescence microscopy. Microtubules moved with brightly fluorescent seeds leading, indicating that the immobilized TL-γ protein was moving toward microtubule plus ends. No movement was observed in the absence of TL-γ. This experiment demonstrates that Tl-γ has plus-ended microtubule motor activity.

---

What is claimed is:

1. A method for identifying an agent as binding to SEQ ID NO:1, comprising:
   (a) contacting a sample that comprises an agent with an amino acid sequence comprising SEQ ID NO:1, wherein said contacting is under conditions for binding said agent to said amino acid sequence; and
   (b) detecting binding of said agent to said SEQ ID NO:1, thereby identifying said agent as binding to SEQ ID NO:1.

2. The method of claim 1, wherein said amino acid sequence comprising SEQ ID NO:1 is immobilized on a support selected from the group consisting of microtiter plate, array, membrane, and bead.

3. The method of claim 1, wherein said amino acid sequence comprising SEQ ID NO:1 is immobilized on a support comprising glass, plastic, polysaccharide, nylon, and nitrocellulose.

4. The method of claim 1, wherein said agent is a protein.

5. The method of claim 1, wherein said agent is an oligonucleotide.

6. A method for identifying an agent as binding to amino acids 1 to 357 of SEQ ID NO:1, comprising:
   (a) contacting a sample that comprises an agent with an amino acid sequence comprising amino acids 1 to 357 of SEQ ID NO:1, wherein said contacting is under conditions for binding said agent to said amino acid sequence; and
   (b) detecting binding of said agent to said amino acid sequence, thereby identifying said agent as binding to amino acids 1 to 357 of SEQ ID NO:1.

7. The method of claim 6, wherein said amino acid sequence comprising amino acids 1 to 357 of SEQ ID NO:1 is immobilized on a support selected from the group consisting of microtiter plate, array, membrane, and bead.

8. The method of claim 6, wherein said amino acid sequence comprising amino acids 1 to 357 of SEQ ID NO:1 is immobilized on a support comprising glass, plastic, polysaccharide, nylon, and nitrocellulose.

9. The method of claim 6, wherein said agent is a protein.

10. The method of claim 6, wherein said agent is an oligonucleotide.

11. A method for identifying an agent as binding to amino acids 443 to 601 of SEQ ID NO:1, comprising:
   (a) contacting a sample that comprises an agent with an amino acid sequence comprising amino acids 443 to 601 of SEQ ID NO:1, wherein said contacting is under conditions for binding said agent to said amino acid sequence; and
   (b) detecting binding of said agent to said amino acid sequence, thereby identifying said agent as binding to amino acids 443 to 601 of SEQ ID NO:1.

12. The method of claim 11, wherein said amino acid sequence comprising amino acids 443 to 601 of SEQ ID NO:1 is immobilized on a support selected from the group consisting of microtiter plate, array, membrane, and bead.

13. The method of claim 11, wherein said amino acid sequence comprising amino acids 443 to 601 of SEQ ID NO:1 is immobilized on a support comprising glass, plastic, polysaccharide, nylon, and nitrocellulose.

14. The method of claim 11, wherein said agent is a protein.

15. The method of claim 11, wherein said agent is an oligonucleotide.

16. The method for identifying an agent as binding to amino acids 602 to 784 of SEQ ID NO:1, comprising:
   (a) contacting a sample that comprises an agent with an amino acid sequence comprising amino acids 602 to 784 SEQ ID NO:1, wherein said contacting is under conditions for binding said agent to said amino acid sequence; and
   (b) detecting binding of said agent to said amino acid sequence, thereby identifying said agent as binding to amino acids 602 to 784 of SEQ ID NO:1.

17. The method of claim 16, wherein said agent said sequence comprising amino acids 602 to 784 of SEQ ID NO:1 is immobilized on a support from the group consisting of microtiter plate, array, membrane, and bead.

18. The method of claim 16, wherein said agent said sequence comprising amino acids 602 to 784 of SEQ ID NO:1 is immobilized on a support comprising glass, plastic, polysaccharide, nylon, and nitrocellulose.

19. The method of claim 16, wherein said agent is a protein.

20. The method of claim 16, wherein said agent is an oligonucleotide.

* * * * *

UNITED STATES PATENT AND TRADEMARK OFFICE
CERTIFICATE OF CORRECTION

PATENT NO. : 6,815,169 B1
DATED : November 9, 2004
INVENTOR(S) : Sakowicz et al.

It is certified that error appears in the above-identified patent and that said Letters Patent is hereby corrected as shown below:

Column 50,
Line 36, please delete "The method" and insert -- A method --.
Lines 46 and 50, please delete "agent said" and insert -- amino acid --.

Signed and Sealed this

Seventeenth Day of May, 2005

JON W. DUDAS
*Director of the United States Patent and Trademark Office*